US012622914B2

(12) United States Patent
Surman et al.

(10) Patent No.: US 12,622,914 B2
(45) Date of Patent: May 12, 2026

(54) PHARMACEUTICAL RECTAL SUPPOSITORY COMPOSITIONS OF 6-THIOGUANINE, METHODS OF TREATMENT AND/OR METHODS OF MANUFACTURING

(71) Applicant: Douglas Pharmaceuticals Ltd., Lincoln (NZ)

(72) Inventors: Peter William Surman, Lincoln (NZ); Zhen Shi, Lincoln (NZ); Fergus Cameron Binnie, Lincoln (NZ); Christopher Ritchie, Lincoln (NZ); Yuefeng Long, Lincoln (NZ)

(73) Assignee: Douglas Pharmaceuticals Ltd., Lincoln (NZ)

( * ) Notice: Subject to any disclaimer, the term of this patent is extended or adjusted under 35 U.S.C. 154(b) by 0 days.

(21) Appl. No.: 18/814,130

(22) Filed: Aug. 23, 2024

(65) Prior Publication Data

US 2025/0064816 A1 Feb. 27, 2025

(30) Foreign Application Priority Data

Aug. 24, 2023 (AU) ................................ 2023902710
Jun. 7, 2024 (AU) ................................ 2024901720

(51) Int. Cl.

| | |
|---|---|
| ***A01N 43/00*** | (2006.01) |
| ***A01N 43/46*** | (2006.01) |
| ***A61K 9/00*** | (2006.01) |
| ***A61K 9/02*** | (2006.01) |
| ***A61K 31/52*** | (2006.01) |
| ***A61K 31/55*** | (2006.01) |
| ***A61K 47/02*** | (2006.01) |
| ***A61K 47/26*** | (2006.01) |
| ***A61K 47/44*** | (2017.01) |
| ***A61P 1/00*** | (2006.01) |

(52) U.S. Cl.
CPC ............ *A61K 31/52* (2013.01); *A61K 9/0031* (2013.01); *A61K 9/02* (2013.01); *A61K 47/02* (2013.01); *A61K 47/26* (2013.01); *A61K 47/44* (2013.01); *A61P 1/00* (2018.01)

(58) Field of Classification Search
None
See application file for complete search history.

(56) References Cited

U.S. PATENT DOCUMENTS

| | | | |
|---|---|---|---|
| 2013/0005749 A1 | 1/2013 | Florin et al. | |
| 2021/0393638 A1 | 12/2021 | Florin et al. | |

FOREIGN PATENT DOCUMENTS

| | | | |
|---|---|---|---|
| AU | 2016333150 A1 | 3/2018 | |
| EP | 2098236 | 9/2009 | |
| JP | 2004501185 A5 * | 1/2004 | |
| WO | 9630021 | 10/1996 | |
| WO | 2000069520 | 11/2000 | |
| WO | 2017054042 | 4/2017 | |
| WO | 2023182895 | 9/2023 | |

OTHER PUBLICATIONS

Crouwel et al. (Rectally Administrated Thioguanine for Distal Ulcerative Colitis: A Multicenter Case Series. Inflamm Bowel Dis. Jun. 1, 2023;29(6):1000-1004. doi: 10.1093/ibd/izac 195. PMID: 36099056; PMCID: PMC10233394.).*

Bayoumy et al. (2020) "The continuous rediscovery and the benefit-risk ratio of thioguanine, a comprehensive review" Expert Opinion on Drug Metabolism & Toxicology 16(2):111-123, DOI: 10.1080/17425255.2020.1719996.

Bayoumy et al. (2021) "Advances in Thiopurine Drug Delivery: The Current State-of-the-Art" European Journal of Drug Metabolism and Pharmacokinetics 46:743-758.

Bayoumy et al. (2020) "Efficacy, safety and drug survival of thioguanine as maintenance treatment for inflammatory bowel disease: a retrospective multi-centre study in the United Kingdom" BMC Gastroenterology 20:296.

Bewtra et al. (2014) "An Optimized Patient-reported Ulcerative Colitis Disease Activity Measure Derived from the Mayo Score and the Simple Clinical Colitis Activity Index" Inflamm Bowel Dis. 20(6):1070-1078.

Crouwel et al. (2023) "Rectally Administered Thioguanine for Distal Ulcerative Colitis: A Multicenter Case Series" Inflammatory Bowel Diseases 29(6):1000-1004.

Florin et al. (2019) "A well-tolerated and rapidly acting thiopurine for IBD?" Drug Discovery Today 24(1):37-41.

Hua (2019) "Physiological and Pharmaceutical Considerations for Rectal Drug Formulations" Frontiers in Pharmacology 10:1196.

Ikeya et al. (2016) "The Ulcerative Colitis Endoscopic Index of Severity More Accurately Reflects Clinical Outcomes and Long-term Prognosis than the Mayo Endoscopic Score" J Crohns Colitis. 10(3):286-295.

Khan et al. (2019) "New Zealand Society of Gastroenterology Guidelines on Therapeutic Drug Monitoring in Inflammatory Bowel Disease" New Zealand Medical Association Journal (NZMJ) 132(1491):46-62.

(Continued)

*Primary Examiner* — Layla Soroush
(74) *Attorney, Agent, or Firm* — FisherBroyles, LLP; Cara L. Crowley-Weber; Christy G. Rothwell

(57) ABSTRACT

Described is a rectal suppository. The rectal suppository comprises 6-thioguanine, at least one hard fat, and at least one surfactant. Further or alternatively, the rectal suppository comprises about 1 to 9 mg of 6-thioguanine. Further or alternatively, there is described a method of preventing, treating and/or managing inflammatory bowel disease in a subject. The method comprises administering a rectal suppository to the subject in need thereof. Further or alternatively, there is described a method of manufacturing a rectal suppository. The method comprises the steps of (a) heating a hard fat to become a liquid hard fat, (b) adding at least one surfactant to the liquid hard fat, (c) adding 6-thioguanine to the liquid hard fat, (d) forming the hard fat into a rectal suppository. Step (b) is optionally carried out before step (c) or after step (c).

17 Claims, 7 Drawing Sheets

(56) References Cited

OTHER PUBLICATIONS

Realdon et al. (2008) “Effects of surfactant characteristics on drug availability from suppositories” Die Pharmazie 63:459-463.

Trial registered on ANZCTR (Australian New Zealand Clinical Trials Registry)—date submitted Apr. 17, 2016, date registered Oct. 5, 2016, Title “Thioguanine Suppositories for Proctitis. An Open Label Phase I Study to Evaluate the Efficacy and Safety of TG as a suppository”, Principle investigator Prof Tim Florin, https://www.anzctr.org.au/Trial/Registration/TrialReview.aspx?id=370532&isReview=true.

Trial registered on ANZCTR (Australian New Zealand Clinical Trials Registry)—date submitted Sep. 6, 2022, date registered Jun. 30, 2022, Title “Tissue concentrations of thioguanine in rectal tissue samples in patients administered thioguanine rectally”, Funding source Douglas Pharmaceuticals, Principle investigator Prof Murray Barclay, https://www.anzctr.org.au/Trial/Registration/TrialReview.aspx?id=384195&isReview=true.

Trial registered on ANZCTR (Australian New Zealand Clinical Trials Registry)—date submitted Sep. 10, 2023, date registered Dec. 19, 2023, Title “Concentrations of Thioguanine and its metabolite 6TGN in Blood and Rectal Tissue Samples in Patients with refractory Ulcerative Proctitis Administered Thioguanine by Suppository”, Funding source Douglas Pharmaceuticals, Principle investigator Prof Murray Barclay. https://www.anzctr.org.au/Trial/Registration/TrialReview.aspx?id=386721&isReview=true.

Van Os et al. (1996) “Azathioprine pharmacokinetics after intravenous, oral, delayed release oral and rectal foam administration” Gut 39:63-68.

* cited by examiner

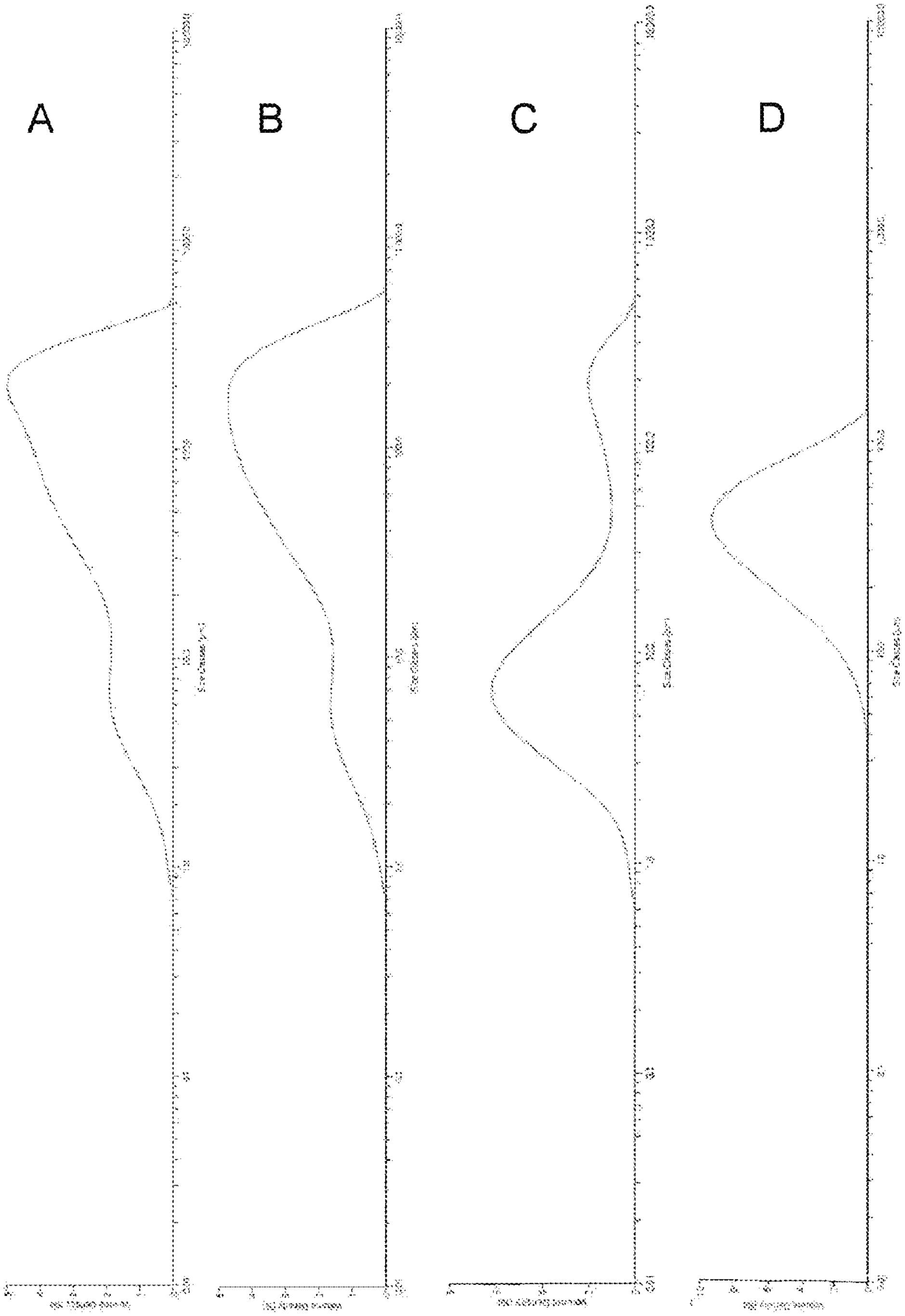
FIGURE 6A-D

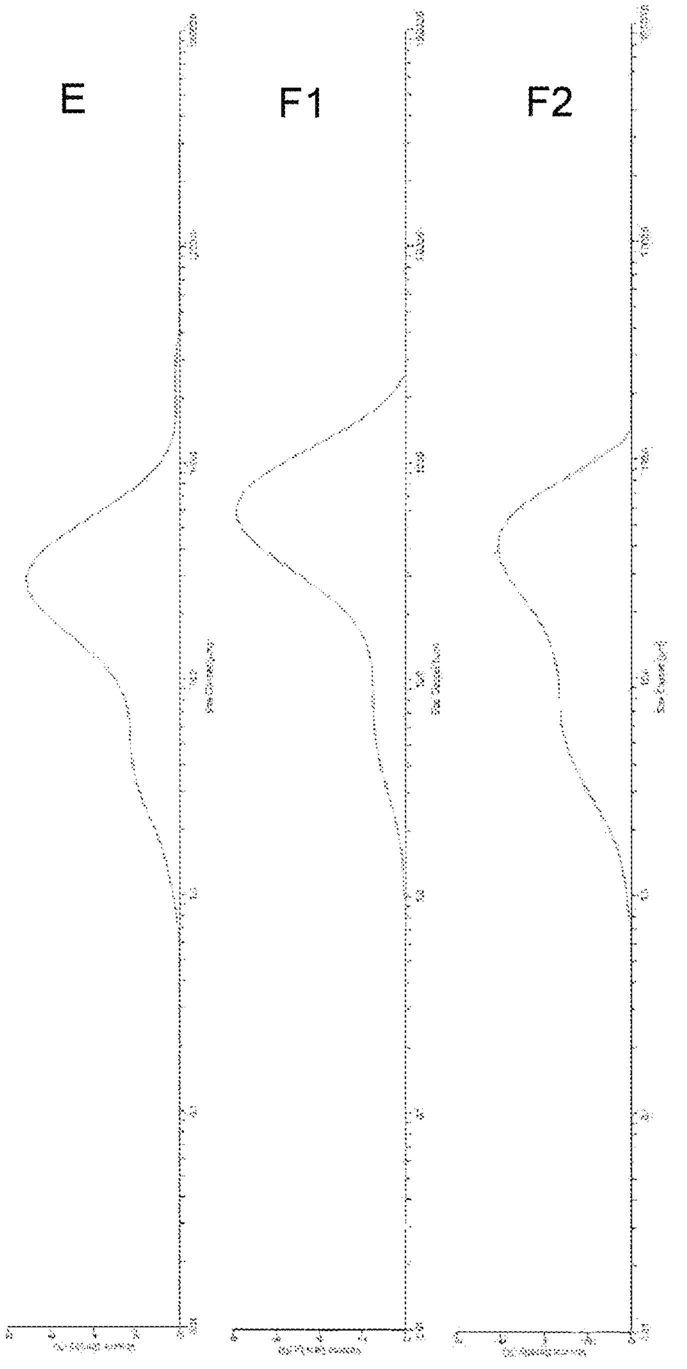
FIGURE 6 E-F2

PHARMACEUTICAL RECTAL SUPPOSITORY COMPOSITIONS OF 6-THIOGUANINE, METHODS OF TREATMENT AND/OR METHODS OF MANUFACTURING

CROSS-REFERENCE TO RELATED APPLICATIONS

This application claims the benefit of AU2023902710, filed on Aug. 24, 2023, and AU2024901720, filed on Jun. 7, 2024, which are herein specifically incorporated by reference in their entireties.

BACKGROUND 6-thioguanine (6-TG) is principally used to treat acute nonlymphocytic leukemias. The oral immediate release tablets sold under brand names Tabloid™ or Lanvis™ contain 40 mg of 6-thioguanine. Tabloid™ and Lanvis™ are not recommended for maintenance therapy or similar long-term continuous treatments due to the high risk of liver toxicity. Patients being treated with 6-TG must be monitored for indications of liver toxicity. Further, patients with an inherited deficiency of thiopurine methyltransferase (TPMT) or Nudix hydrolase 15 (NUDT15) are at higher risk of toxicity and typically require 10% or less of the standard 6-thioguanine dosage.

Oral 6-thioguanine is sold in the Netherlands under brand name Thiosix™ for treatment of inflammatory bowel disease (Crohn's disease or ulcerative colitis). The daily dose recommended on the label is 0.3 mg per kg of body weight with a maximum dose of 25 mg per day. Each Thiosix™ tablet is 10 mg or 20 mg and has a score line to enable the tablet to be divided into two doses. Tabloid™ and Lanvis™ are also used off label in other countries to treat inflammatory bowel disease but are not registered for this use.

Crouwel F, Simsek M, van Doorn A S, Mulder C J J, Buiter H J C, Barclay M L, Florin T H, de Boer-N K. "Rectally Administrated Thioguanine for Distal Ulcerative Colitis: A Multicenter Case Series", Inflammatory Bowel Diseases, Volume 29, Issue 6, June 2023, pages 1000-1004, describes use of 20 mg thioguanine enemas and rectal suppositories to treat proctitis and left-sided colitis. The rectal suppositories were prescribed on an individual basis under a special access scheme in Australia, which is available where no alternative drug formulation is licensed. The 20 mg rectal suppositories were made and dispensed by licensed compounding pharmacies using Good Manufacturing Practice thioguanine and excipients. The paper does not disclose the excipients used in the rectal suppositories. However, Timothy Florin (University of Queensland), one of the authors of the paper, has confirmed the sole ingredients of the rectal suppositories were 6-thioguanine and cocoa butter. The 6-thioguanine was sieved using 40 #sieve prior to combining with the melted cocoa butter. 40 #sieve is equivalent to 400 μm, so the thioguanine had a particle size no larger than 400 μm.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY

In a first aspect there is provided a rectal suppository comprising:

6-thioguanine, at least one hard fat, and at least one surfactant.

In one aspect there is provided a rectal suppository comprising about 1 to 9 mg of 6-thioguanine.

In one aspect there is provided a rectal suppository comprising about 1 to 9 mg of 6-thioguanine and at least one hard fat.

In one aspect there is provided a rectal suppository comprising about 1 to 9 mg of 6-thioguanine, at least one hard fat, and at least one surfactant.

In at least one example, the suppository comprises about 1 to 30 mg of 6-thioguanine. In at least one example, the suppository comprises about 3 to 25 mg of 6-thioguanine. In at least one example, the suppository comprises about 5 to 20 mg of 6-thioguanine.

In at least one example, the suppository comprises about 8 to 30 mg of 6-thioguanine. In at least one example, the suppository comprises about 8 to 25 mg of 6-thioguanine. In at least one example, the suppository comprises about 10 to 20 mg of 6-thioguanine.

In at least one example, the suppository comprises about 15 to 30 mg of 6-thioguanine. In at least one example, the suppository comprises about 17 to 25 mg of 6-thioguanine. In at least one example, the suppository comprises about 20 mg of 6-thioguanine.

In at least one example, the suppository comprises about 6 to 15 mg of 6-thioguanine. In at least one example, the suppository comprises about 8 to 12 mg of 6-thioguanine. In at least one example, the suppository comprises about 10 mg of 6-thioguanine.

In at least one example, the suppository comprises about 1 to 9 mg of 6-thioguanine. In at least one example, the suppository comprises about 2 to 9 mg of 6-thioguanine. In at least one example, the suppository comprises about 3 to 9 mg of 6-thioguanine. In at least one example, the suppository comprises about 3 to 7 mg of 6-thioguanine. In at least one example, the suppository comprises about 4 to 6 mg of 6-thioguanine. In at least one example, the suppository comprises about 5 mg of 6-thioguanine.

In at least one example, the suppository comprises about 0.05 to 5% w/w of 6-thioguanine. In at least one example, the suppository comprises about 0.05 to 3% w/w of 6-thioguanine. In at least one example, the suppository comprises about 0.05 to 2.5% w/w of 6-thioguanine. In at least one example, the suppository comprises about 0.05 to 2% w/w of 6-thioguanine. In at least one example, the suppository comprises about 0.2 to 1.5% w/w of 6-thioguanine. In at least one example, the suppository comprises about 0.3 to 1.1% w/w of 6-thioguanine.

In at least one example, the suppository comprises about 0.4 to 2% w/w of 6-thioguanine. In at least one example, the suppository comprises about 0.4 to 1.5% w/w of 6-thioguanine. In at least one example, the suppository comprises about 0.5 to 1.1% w/w of 6-thioguanine.

In at least one example, the suppository comprises about 0.6 to 2% w/w of 6-thioguanine. In at least one example, the suppository comprises about 0.7 to 1.5% w/w of 6-thioguanine. In at least one example, the suppository comprises about 0.8 to 1.1% w/w of 6-thioguanine. In at least one example, the suppository comprises about 1.1% w/w of 6-thioguanine.

In at least one example, the suppository comprises about 0.4 to 1.0% w/w of 6-thioguanine. In at least one example, the suppository comprises about 0.4 to 0.9% w/w of 6-thioguanine. In at least one example, the suppository comprises about 0.4 to 0.8% w/w of 6-thioguanine. In at least one example, the suppository comprises about 0.5% w/w of 6-thioguanine.

In at least one example, the suppository comprises about 0.05 to 0.4% w/w of 6-thioguanine. In at least one example, the suppository comprises about 0.1 to 0.4% w/w of 6-thioguanine. In at least one example, the suppository comprises about 0.2 to 0.4% w/w of 6-thioguanine. In at least one example, the suppository comprises about 0.3% w/w of 6-thioguanine.

In at least one example, the 6-thioguanine in the suppository has a particle size distribution of D50 of less than about 100 μm. In at least one example, the 6-thioguanine in the suppository has a particle size distribution of D50 of less than about 80 μm. In at least one example, the 6-thioguanine in the suppository has a particle size distribution of D50 of less than about 60 μm. In at least one example, the 6-thioguanine in the suppository has a particle size distribution of D50 of less than about 40 μm. In at least one example, the 6-thioguanine in the suppository has a particle size distribution of D50 of less than about 30 μm. In at least one example, the 6-thioguanine in the suppository has a particle size distribution of D50 of less than about 20 μm.

In at least one example, the 6-thioguanine in the suppository has a particle size distribution of D50 of about 1 to 100 μm. In at least one example, the 6-thioguanine in the suppository has a particle size distribution of D50 of about 1 to 80 μm. In at least one example, the 6-thioguanine in the suppository has a particle size distribution of D50 of about 1 to 60 μm. In at least one example, the 6-thioguanine in the suppository has a particle size distribution of D50 of about 1 to 40 μm. In at least one example, the 6-thioguanine in the suppository has a particle size distribution of D50 of about 1 to 30 μm. In at least one example, the 6-thioguanine in the suppository has a particle size distribution of D50 of about 1 to 20 μm.

In at least one example, the suppository comprises at least one hard fat.

In at least one example, the suppository comprises about 80 to 99.9% w/w hard fat. In at least one example, the suppository comprises about 85 to 99.5% w/w hard fat. In at least one example, the suppository comprises about 90 to 99.5% w/w hard fat. In at least one example, the suppository comprises about 95 to 99.5% w/w hard fat.

In at least one example, the hard fat comprises mono-, di- and/or triglyceride esters of C10 to C18 fatty acids.

In at least one example, the hard fat comprises mono-, di- and triglyceride esters of C10 to C18 fatty acids.

In at least one example, the hard fat comprises mono-, di- and triglyceride esters of C10 to C18 fatty acids, with the triglyceride esters being predominant.

In at least one example, the hard fat comprises less than about 10 mole % of one or more unsaturated fatty acid(s). In at least one example, the hard fat comprises less than about 5 mole % of one or more unsaturated fatty acid(s). In at least one example, the hard fat comprises less than about 2 mole % of one or more unsaturated fatty acid(s). In at least one example, the hard fat comprises less than about 1 mole % of one or more unsaturated fatty acid(s).

In at least one example, the esters were made by inter-esterification of hydrogenated palm oil and hydrogenated palm kernel oil.

In at least one example, the hard fat has a hydroxyl value of less than 40 mg KOH/g. In at least one example, the hard fat has a hydroxyl value of about 1 to 35 mg KOH/g. In at least one example, the hard fat has a hydroxyl value of about 1 to 30 mg KOH/g.

In at least one example, the hard fat has a melting range of about 34 to 38° C. In at least one example, the hard fat has a melting range of about 34 to 36° C.

In at least one example, the suppository comprises at least one surfactant.

In at least one example, the surfactant has a hydrophilic-lipophilic balance (HLB) value of equal to or greater than about 10.

In at least one example, the surfactant is non-ionic.

In at least one example, the surfactant is selected from any one or more of a polysorbate, a polyoxyethylene derivative of natural or hydrogenated vegetable oil(s), a alkyl/dialykyl sulfate, sulfonate or sulfosuccinate salt, a polyoxyethylene fatty acid ester, a phospholipid, a transesterification product of natural vegetable oil triglyceride and polyalkylene polyol, a sorbitan fatty acid ester, a pentaerythritol fatty acid ester, a polyoxyethylene glycol alkyl ether and/or ester, a sucrose ester, an ethoxylated fatty alcohol, a fatty acid salt.

In at least one example, the surfactant has a melting point below 35° C.

In at least one example, the surfactant is polysorbate 80.

In at least one example, the suppository comprises about 0.1 to 20% w/w surfactant. In at least one example, the suppository comprises about 0.1 to 15% w/w surfactant. In at least one example, the suppository comprises about 0.1 to 10% w/w surfactant. In at least one example, the suppository comprises about 0.1 to 5% w/w surfactant. In at least one example, the suppository comprises about 0.2 to 3% w/w surfactant. In at least one example, the suppository comprises about 0.4 to 3% w/w surfactant. In least one example, the suppository comprises about 0.5 to 3% w/w surfactant. In least one example, the suppository comprises about 0.5 to 2% w/w surfactant.

In at least one example, the suppository comprises about 0.1 to 5% w/w polysorbate 80. In at least one example, the suppository comprises about 0.2 to 3% w/w polysorbate 80. In at least one example, the suppository comprises about 0.4 to 3% w/w polysorbate 80. In least one example, the suppository comprises about 0.5 to 3% w/w polysorbate 80. In least one example, the suppository comprises about 0.5 to 2% w/w polysorbate 80. In least one example, the suppository comprises about 0.5 to 1.5% w/w polysorbate 80.

In at least one example, the suppository comprises a suspending agent.

In at least one example, the suspending agent is present in a range of about 0.05 to 10% w/w, or about 0.1 to 5% w/w, or about 0.1 to 4% w/w, or about 0.1 to 3% w/w, or about 0.1 to 2% w/w, or about 0.1 to 1% w/w.

In at least one example, the suspending agent is selected from one or more of: silicon dioxide, a clay (including purified and/or refined clays), aluminum monostearate and magnesium stearate.

In at least one example, the clay is selected from one or more of kaolin, palygorskite, smectites, sylvite, bentonite, halite, and magnesium aluminum silicate.

In at least one example, the suspending agent comprises silicon dioxide.

In at least one example, the silicon dioxide is fumed silica and/or colloidal silica.

In at least one example, the silicon dioxide is present in a range of about 0.05 to 10% w/w, or about 0.1 to 5% w/w, or about 0.1 to 4% w/w, or about 0.1 to 3% w/w, or about 0.1 to 2% w/w, or about 0.1 to 1% w/w.

In at least one example, the suppository comprises an antioxidant.

In at least one example, the antioxidant is selected from the group consisting of butylated hydroxyanisole (BHA), butylated hydroxytoluene (BHT), propyl gallate, tocopherols (e.g., α-tocopherol (vitamin E)), propionic acid, sodium nitrate, sodium nitrite, an anthocyanin, citric acid (for example citric acid monohydrate) and combinations thereof.

In at least one example, the antioxidant comprises butylated hydroxyanisole (BHA).

In at least one example, the antioxidant comprises vitamin E.

In at least one example, the antioxidant comprises butylated hydroxyanisole (BHA) and vitamin E.

In at least one example, the antioxidant is present in a range of about 0.0003 to 8%, or about 0.003 to 4% w/w, or about 0.003 to 2.5% w/w.

In at least one example, the suppository comprises: about 1 to 30 mg of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 8 to 30 mg of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 15 to 30 mg of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 6 to 15 mg of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 1 to 9 mg of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 0.05 to 5% w/w of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 0.05 to 2% w/w of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 0.4 to 2% w/w of the 6-thioguanine, about 80 to 99.5% w/w of the hard fat, about 0.1 to 20% w/w of the at least one surfactant, optionally at least one suspending agent, and optionally at least one antioxidant.

In at least one example, the suppository comprises: about 0.6 to 2% w/w of the 6-thioguanine, about 80 to 99.3% w/w of the hard fat, about 0.1 to 20% w/w of the at least one surfactant, optionally at least one suspending agent, and optionally at least one antioxidant.

In at least one example, the suppository comprises: about 0.4 to 1% w/w of the 6-thioguanine, about 80 to 99.5% w/w of the hard fat, about 0.1 to 20% w/w of the at least one surfactant, optionally at least one suspending agent, and optionally at least one antioxidant.

In at least one example, the suppository comprises: about 0.05 to 0.4% w/w of the 6-thioguanine, about 80 to 99.9% w/w of the hard fat, about 0.1 to 20% w/w of the at least one surfactant, optionally at least one suspending agent, and optionally at least one antioxidant.

In at least one example, the suppository comprises: about 0.05 to 2% w/w of the 6-thioguanine, about 80 to 99.8% w/w of the hard fat, about 0.1 to 20% w/w of the at least one surfactant, about 0.05 to 10% w/w of at least one suspending agent, and optionally at least one antioxidant.

In at least one example, the suppository comprises: about 0.4 to 2% w/w of the 6-thioguanine, about 80 to 99.5% w/w of the hard fat, about 0.1 to 20% w/w of the at least one surfactant, about 0.05 to 10% w/w of at least one suspending agent, and optionally at least one antioxidant.

In at least one example, the suppository comprises: about 0.6 to 2% w/w of the 6-thioguanine, about 80 to 99.3% w/w of the hard fat, about 0.1 to 20% w/w of the at least one surfactant, about 0.05 to 10% w/w of at least one suspending agent, and optionally at least one antioxidant.

In at least one example, the suppository comprises: about 0.4 to 1% w/w of the 6-thioguanine, about 80 to 99.5% w/w of the hard fat, about 0.1 to 20% w/w of the at least one surfactant, about 0.05 to 10% w/w of at least one suspending agent, and optionally at least one antioxidant.

In at least one example, the suppository comprises: about 0.05 to 0.4% w/w of the 6-thioguanine, about 80 to 99.8% w/w of the hard fat, about 0.1 to 20% w/w of the at least one surfactant, about 0.05 to 10% w/w of at least one suspending agent, and optionally at least one antioxidant.

In at least one example, the suppository has a total weight of about 800 to 3000 mg. In at least one example, the suppository has a total weight of about 1000 to 3000 mg. In at least one example, the suppository has a total weight of about 1200 to 3000 mg. In at least one example, the suppository has a total weight of about 1500 to 3000 mg. In at least one example, the suppository has a total weight of about 1800 to 2200 mg. In at least one example, the suppository has a total weight of about 1800 to 2000 mg. In at least one example, the suppository has a total weight of about 1000 to 2500 mg. In at least one example, the suppository has a total weight of about 1000 to 2000 mg.

In at least one example, the suppository has a melting range of about 33 to 38° C. In at least one example, the suppository has a melting range of about 33 to 37° C. In at least one example, the suppository has a melting range of about 33 to 36° C.

In at least one example, the suppository exhibits release of the 6-thioguanine in vitro in dissolution medium that substantially corresponds to about 40 to 100%, or about 50 to 100%, or about 60 to 100%, or about 70 to 100% of the 6-thioguanine at about 20 minutes from placement of the suppository in the dissolution medium.

In at least one example, the suppository exhibits release of the 6-thioguanine in vitro in dissolution medium that substantially corresponds to about 40 to 100%, or about 50 to 100%, or about 60 to 100%, or about 70 to 100%, or about 80 to 100% of the 6-thioguanine at about 30 minutes from placement of the suppository in the dissolution medium.

In at least one example, the suppository exhibits release of the 6-thioguanine in vitro in dissolution medium that substantially corresponds to about 80 to 100%, or about 85 to 100%, or about 90 to 100%, of the 6-thioguanine at about 60 minutes from placement of the suppository in the dissolution medium.

In at least one example, the suppository exhibits release of the 6-thioguanine in vitro in dissolution medium that substantially corresponds to not less than about 40%, or not less than about 60%, or not less than about 80%, of the 6-thioguanine at about 60 minutes from placement of the suppository in the dissolution medium.

In at least one example, the suppository exhibits release of the 6-thioguanine in vitro in dissolution medium that substantially corresponds to:

(a) about 20 to 100% of the 6-thioguanine at about 20 minutes from placement of the suppository in the dissolution medium.

(b) not less than about 40% of the 6-thioguanine at about 60 minutes from placement of the suppository in the dissolution medium.

In at least one example, the suppository exhibits release of the 6-thioguanine in vitro in dissolution medium that substantially corresponds to:

(a) about 30 to 100% of the 6-thioguanine at about 20 minutes from placement of the suppository in the dissolution medium.

(b) not less than about 60% of the 6-thioguanine at about 60 minutes from placement of the suppository in the dissolution medium.

In at least one example, the suppository exhibits release of the 6-thioguanine in vitro in dissolution medium that substantially corresponds to:

(a) about 40 to 100% of the 6-thioguanine at about 20 minutes from placement of the suppository in the dissolution medium.

(b) not less than about 80% of the 6-thioguanine at about 60 minutes from placement of the suppository in the dissolution medium.

In at least one example, the suppository exhibits release of the 6-thioguanine in vitro in dissolution medium that substantially corresponds to:

(a) about 60 to 100% of the 6-thioguanine at about 20 minutes from placement of the suppository in the dissolution medium.

(b) not less than about 80% of the 6-thioguanine at about 60 minutes from placement of the suppository in the dissolution medium.

In at least one example, the suppository provides mean 6-TGN levels of less than about 150 pmol/8×$10^8$ RBC 6 hours after administration of the suppository.

In at least one example, the suppository provides mean 6-TGN levels of less than about 100 pmol/8×$10^8$ RBC 6 hours after administration of the suppository.

In at least one example, the suppository provides mean 6-TGN levels of less than about 75 pmol/8×$10^8$ RBC 6 hours after administration of the suppository.

In at least one example, the suppository provides mean 6-TGN levels of less than about 60 pmol/8×$10^8$ RBC 6 hours after administration of the suppository.

In at least one example, the suppository provides mean 6-TGN levels of less than about 30 pmol/8×$10^8$ RBC 6 hours after administration of the suppository.

In at least one example, the suppository provides mean 6-TGN levels of less than about 25 pmol/8×$10^8$ RBC 6 hours after administration of the suppository.

In at least one example, the suppository provides mean 6-TGN levels of less than about 20 pmol/8×$10^8$ RBC 6 hours after administration of the suppository.

In at least one example, the suppository provides low 6-TGN and/or 6-TG levels in breast milk in the subject while the suppository is administered once a day to the subject.

In at least one example, the suppository provides levels 6-TGN and/or 6-TG in breast milk in the subject at or below 15 ng/ml while the suppository is administered once a day to the subject.

In at least one example, the suppository provides levels 6-TGN and/or 6-TG in breast milk in the subject at or below 10 ng/ml while the suppository is administered once a day to the subject.

In at least one example, the suppository provides levels 6-TGN and/or 6-TG in breast milk in the subject at or below 5 ng/ml while the suppository is administered once a day to the subject.

In at least one example, the suppository provides levels 6-TGN and/or 6-TG in breast milk in the subject at or below 2.5 ng/ml while the suppository is administered once a day to the subject.

In at least one example, the suppository provides undetectable levels 6-TGN and/or 6-TG in breast milk in the subject while the suppository is administered once a day to the subject.

In at least one example, the suppository provides levels 6-TGN and/or 6-TG in breast milk in the subject at or below 15 ng/ml while the suppository is administered once a day to the subject for at least 28 days.

In at least one example, the suppository provides levels 6-TGN and/or 6-TG in breast milk in the subject at or below 10 ng/ml while the suppository is administered once a day to the subject for at least 28 days.

In at least one example, the suppository provides levels 6-TGN and/or 6-TG in breast milk in the subject at or below 5 ng/ml while the suppository is administered once a day to the subject for at least 28 days.

In at least one example, the suppository provides levels 6-TGN and/or 6-TG in breast milk in the subject at or below 2.5 ng/ml while the suppository is administered once a day to the subject for at least 28 days.

In at least one example, the suppository provides undetectable levels 6-TGN and/or 6-TG in breast milk in the subject while the suppository is administered once a day to the subject for at least 28 days.

In at least one example, the suppository provides low 6-TGN and/or 6-TG levels in breast milk in the subject while the suppository is administered once a day to the subject, wherein the suppository comprises about 1 to 9 mg of 6-thioguanine.

In at least one example, the suppository provides levels 6-TGN and/or 6-TG in breast milk in the subject at or below 15 ng/ml while the suppository is administered once a day to the subject, wherein the suppository comprises about 1 to 9 mg of 6-thioguanine.

In at least one example, the suppository provides levels 6-TGN and/or 6-TG in breast milk in the subject at or below 10 ng/ml while the suppository is administered once a day to the subject, wherein the suppository comprises about 1 to 9 mg of 6-thioguanine.

In at least one example, the suppository provides levels 6-TGN and/or 6-TG in breast milk in the subject at or below 5 ng/ml while the suppository is administered once a day to the subject, wherein the suppository comprises about 1 to 9 mg of 6-thioguanine.

In at least one example, the suppository provides levels 6-TGN and/or 6-TG in breast milk in the subject at or below 2.5 ng/mL while the suppository is administered once a day to the subject, wherein the suppository comprises about 1 to 9 mg of 6-thioguanine.

In at least one example, the suppository provides undetectable levels 6-TGN and/or 6-TG in breast milk in the subject while the suppository is administered once a day to the subject, wherein the suppository comprises about 1 to 9 mg of 6-thioguanine.

In at least one example, the suppository provides levels 6-TGN and/or 6-TG in breast milk in the subject at or below 15 ng/ml while the suppository is administered once a day to the subject for at least 28 days, wherein the suppository comprises about 1 to 9 mg of 6-thioguanine.

In at least one example, the suppository provides levels 6-TGN and/or 6-TG in breast milk in the subject at or below 10 ng/mL while the suppository is administered once a day to the subject for at least 28 days, wherein the suppository comprises about 1 to 9 mg of 6-thioguanine.

In at least one example, the suppository provides levels 6-TGN and/or 6-TG in breast milk in the subject at or below 5 ng/ml while the suppository is administered once a day to the subject for at least 28 days, wherein the suppository comprises about 1 to 9 mg of 6-thioguanine.

In at least one example, the suppository provides levels 6-TGN and/or 6-TG in breast milk in the subject at or below 2.5 ng/ml while the suppository is administered once a day to the subject for at least 28 days, wherein the suppository comprises about 1 to 9 mg of 6-thioguanine.

In at least one example, the suppository provides undetectable levels 6-TGN and/or 6-TG in breast milk in the subject while the suppository is administered once a day to the subject for at least 28 days, wherein the suppository comprises about 1 to 9 mg of 6-thioguanine.

For the avoidance of doubt, the embodiments and/or examples above may apply alone or in any combination of two or more thereof to any one or more of the aspects set forth below where the context allows.

In one aspect there is provided a method of preventing, treating and/or managing inflammatory bowel disease in a subject, the method comprising administering a rectal suppository as described in the first aspect to the subject in need thereof.

In one aspect there is provided a method of preventing, treating and/or managing inflammatory bowel disease in a subject, the method comprising rectally administering to the subject about 1 to 9 mg 6-thioguanine in the form of a rectal suppository.

In one aspect there is provided use of a rectal suppository comprising 6-thioguanine as described in the first aspect in the manufacture of a medicament for prevention, treatment and/or management of inflammatory bowel disease.

In one aspect there is provided use of a rectal suppository comprising 6-thioguanine in the manufacture of a medicament for prevention, treatment and/or management of inflammatory bowel disease, wherein the suppository comprises about 1 to 9 mg 6-thioguanine.

In one aspect there is provided a rectal suppository comprising 6-thioguanine as described in the first aspect for prevention, treatment and/or management of inflammatory bowel disease.

In one aspect there is provided a rectal suppository comprising 6-thioguanine for prevention, treatment and/or management of inflammatory bowel disease, wherein the suppository comprises about 1 to 9 mg 6-thioguanine.

In one aspect there is provided use of a rectal suppository comprising 6-thioguanine as described in the first aspect for prevention, treatment and/or management of inflammatory bowel disease.

In one aspect there is provided use of a rectal suppository comprising 6-thioguanine for prevention, treatment and/or management of inflammatory bowel disease, wherein the suppository comprises about 1 to 9 mg 6-thioguanine.

In at least one example, the inflammatory bowel disease effects the rectum.

In at least one example, the inflammatory bowel disease is ulcerative colitis or Crohn's disease, effecting the rectum.

In at least one example the ulcerative colitis is ulcerative proctitis, proctosigmoiditis, and/or left-sided colitis.

In at least one example, the suppository is administered once a day or twice a day to the subject.

In at least one example, the suppository is administered once a day to the subject.

In at least one example, the suppository is formulated for once a day administration or twice a day administration to a patient.

In at least one example, the suppository is formulated for once a day administration to a patient.

In at least one example, the suppository provides a dose of 6-thioguanine of about 0.01 to 0.4 mg per kg of body weight.

In at least one example, the suppository provides a daily dose of 6-thioguanine of about 0.01 to 0.4 mg per kg of body weight.

In at least one example, the suppository provides a dose of 6-thioguanine of about 0.1 to 0.4 mg per kg of body weight.

In at least one example, the suppository provides a daily dose of 6-thioguanine of about 0.1 to 0.4 mg per kg of body weight.

In at least one example, the suppository provides a dose of 6-thioguanine of about 0.01 to 0.1 mg per kg of body weight. In at least one example, the suppository provides a dose of 6-thioguanine of 0.01 to 0.09 mg per kg of body weight. In at least one example, the suppository provides a dose of 6-thioguanine of 0.02 to 0.08 mg per kg of body weight. In at least one example, the suppository provides a dose of 6-thioguanine of 0.03 to 0.08 mg per kg of body weight. In at least one example, the suppository provides a dose of 6-thioguanine of 0.04 to 0.08 mg per kg of body weight. In at least one example, the suppository provides a dose of 6-thioguanine of 0.05 to 0.08 mg per kg of body weight.

In at least one example, the suppository provides a daily dose of 6-thioguanine of about 0.01 to 0.1 mg per kg of body weight. In at least one example, the suppository provides a daily dose of 6-thioguanine of 0.01 to 0.09 mg per kg of body weight. In at least one example, the suppository provides a daily dose of 6-thioguanine of 0.02 to 0.08 mg per kg of body weight. In at least one example, the suppository provides a daily dose of 6-thioguanine of 0.03 to 0.08 mg per kg of body weight. In at least one example, the suppository provides a daily dose of 6-thioguanine of 0.04 to 0.08 mg per kg of body weight. In at least one example, the suppository provides a daily dose of 6-thioguanine of 0.05 to 0.08 mg per kg of body weight.

In at least one example, the suppository provides a clinical response in the subject in 8 weeks or less of starting once a day administration of the suppository to the subject.

In at least one example, the suppository provides a clinical response in the subject in 6 weeks or less of starting once a day administration of the suppository to the subject.

In at least one example, the suppository provides a clinical response in the subject in 30 days or less of starting once a day administration of the suppository to the subject.

In at least one example, the suppository provides a clinical response in the subject in 22 days or less of starting once a day administration of the suppository to the subject.

In at least one example, the suppository provides a clinical response in the subject in 8 days or less of starting once a day administration of the suppository to the subject.

In at least one example, the suppository provides a reduction in Simple Clinical Colitis Activity Index (SCCAI) score of 2 or more in the subject in 8 weeks or less of starting once a day administration of the suppository to the subject.

In at least one example, the suppository provides a reduction in Simple Clinical Colitis Activity Index (SCCAI) score of 3 or more in the subject in 8 weeks or less of starting once a day administration of the suppository to the subject.

In at least one example, the suppository provides a reduction in Simple Clinical Colitis Activity Index (SCCAI) score of 4 or more in the subject in 8 weeks or less of starting once a day administration of the suppository to the subject.

In at least one example, the suppository provides a reduction in Simple Clinical Colitis Activity Index (SCCAI) score of 2 or more in the subject in 6 weeks or less of starting once a day administration of the suppository to the subject.

In at least one example, the suppository provides a reduction in Simple Clinical Colitis Activity Index (SCCAI) score of 3 or more in the subject in 6 weeks or less of starting once a day administration of the suppository to the subject.

In at least one example, the suppository provides a reduction in Simple Clinical Colitis Activity Index (SCCAI) score of 4 or more in the subject in 6 weeks or less of starting once a day administration of the suppository to the subject.

In at least one example, the suppository provides a reduction in Simple Clinical Colitis Activity Index (SCCAI) score of 2 or more in the subject in 30 days or less of starting once a day administration of the suppository to the subject.

In at least one example, the suppository provides a reduction in Simple Clinical Colitis Activity Index (SCCAI) score of 3 or more in the subject in 30 days or less of starting once a day administration of the suppository to the subject.

In at least one example, the suppository provides a reduction in Simple Clinical Colitis Activity Index (SCCAI) score of 4 or more in the subject in 30 days or less of starting once a day administration of the suppository to the subject.

In at least one example, the suppository provides a reduction in Simple Clinical Colitis Activity Index (SCCAI) score of 2 or more in the subject in 22 days or less of starting once a day administration of the suppository to the subject.

In at least one example, the suppository provides a reduction in Simple Clinical Colitis Activity Index (SCCAI) score of 3 or more in the subject in 22 days or less of starting once a day administration of the suppository to the subject.

In at least one example, the suppository provides a reduction in Simple Clinical Colitis Activity Index (SCCAI) score of 4 or more in the subject in 22 days or less of starting once a day administration of the suppository to the subject.

In at least one example, the suppository provides a reduction in Simple Clinical Colitis Activity Index (SCCAI) score of 2 or more in the subject in 15 days or less of starting once a day administration of the suppository to the subject.

In at least one example, the suppository provides a reduction in Simple Clinical Colitis Activity Index (SCCAI) score of 3 or more in the subject in 15 days or less of starting once a day administration of the suppository to the subject.

In at least one example, the suppository provides a reduction in Simple Clinical Colitis Activity Index (SCCAI) score of 4 or more in the subject in 15 days or less of starting once a day administration of the suppository to the subject.

In at least one example, the suppository provides a reduction in Simple Clinical Colitis Activity Index (SCCAI) score of 2 or more in the subject in 8 days or less of starting once a day administration of the suppository to the subject.

In at least one example, the suppository provides a reduction in Simple Clinical Colitis Activity Index (SCCAI) score of 3 or more in the subject in 8 days or less of starting once a day administration of the suppository to the subject.

In at least one example, the suppository provides a reduction in Simple Clinical Colitis Activity Index (SCCAI) score of 4 or more in the subject in 8 days or less of starting once a day administration of the suppository to the subject.

In at least one example, the suppository provides remission in the subject in 8 weeks or less of starting once a day administration of the suppository to the subject.

In at least one example, the suppository provides remission in the subject in 6 weeks or less of starting once a day administration of the suppository to the subject.

In at least one example, the suppository provides remission in the subject in 30 days or less of starting once a day administration of the suppository to the subject.

In at least one example, the suppository provides remission in the subject in 22 days or less of starting once a day administration of the suppository to the subject.

In at least one example, the suppository provides remission in the subject in 15 days or less of starting once a day administration of the suppository to the subject.

In at least one example, the suppository provides remission in the subject in 8 days or less of starting once a day administration of the suppository to the subject.

In at least one example, the suppository provides remission in the subject in 8 weeks or less of starting once a day administration of the suppository to the subject, wherein the suppository comprises about 5 mg of 6-thioguanaine.

In at least one example, the suppository provides remission in the subject in 6 weeks or less of starting once a day administration of the suppository to the subject, wherein the suppository comprises about 5 mg of 6-thioguanaine.

In at least one example, the suppository provides remission in the subject in 30 days or less of starting once a day administration of the suppository to the subject, wherein the suppository comprises about 5 mg of 6-thioguanaine.

In at least one example, the suppository provides remission in the subject in 22 days or less of starting once a day administration of the suppository to the subject, wherein the suppository comprises about 5 mg of 6-thioguanaine.

In at least one example, the suppository provides remission in the subject in 15 days or less of starting once a day administration of the suppository to the subject, wherein the suppository comprises about 5 mg of 6-thioguanaine.

In at least one example, the suppository provides remission in the subject in 8 days or less of starting once a day administration of the suppository to the subject, wherein the suppository comprises about 5 mg of 6-thioguanaine.

In at least one example, the suppository provides a reduction in Simple Clinical Colitis Activity Index (SCCAI) score in the subject from a score greater than 2 to a score equal to or less than 2, with a reduction in the score of greater than or equal to 3, in 8 weeks or less of starting once a day administration of the suppository to the subject.

In at least one example, the suppository provides a reduction in Simple Clinical Colitis Activity Index (SCCAI) score in the subject from a score greater than 2 to a score equal to or less than 2, with a reduction in the score of greater than or equal to 3, in 6 weeks or less of starting once a day administration of the suppository to the subject.

In at least one example, the suppository provides a reduction in Simple Clinical Colitis Activity Index (SCCAI) score in the subject from a score greater than 2 to a score equal to or less than 2, with a reduction in the score of greater than or equal to 3, in 30 days or less of starting once a day administration of the suppository to the subject.

In at least one example, the suppository provides a reduction in Simple Clinical Colitis Activity Index (SCCAI) score in the subject from a score greater than 2 to a score equal to or less than 2, with a reduction in the score of greater than or equal to 3, in 22 days or less of starting once a day administration of the suppository to the subject.

In at least one example, the suppository provides a reduction in Simple Clinical Colitis Activity Index (SCCAI) score in the subject from a score greater than 2 to a score equal to or less than 2, with a reduction in the score of greater than or equal to 3, in 15 days or less of starting once a day administration of the suppository to the subject.

In at least one example, the suppository provides a reduction in Simple Clinical Colitis Activity Index (SCCAI) score in the subject from a score greater than 2 to a score equal to or less than 2, with a reduction in the score of greater than or equal to 3, in 8 days or less of starting once a day administration of the suppository to the subject, In at least one example, the suppository provides a reduction in Mayo Endoscopic Score (Mayo ES) in the subject of at least 1 point in 8 weeks or less of starting once a day administration of the suppository to the subject.

In at least one example, the suppository provides a reduction in Mayo Endoscopic Score (Mayo ES) in the subject of at least 1 point in 6 weeks or less of starting once a day administration of the suppository to the subject.

In at least one example, the suppository provides a reduction in Mayo Endoscopic Score (Mayo ES) in the subject of at least 1 point in 30 days or less of starting once a day administration of the suppository to the subject.

In at least one example, the suppository provides a reduction in Mayo Endoscopic Score (Mayo ES) in the subject of at least 2 points in 8 weeks or less of starting once a day administration of the suppository to the subject.

In at least one example, the suppository provides a reduction in Mayo Endoscopic Score (Mayo ES) in the subject of at least 2 points in 6 weeks or less of starting once a day administration of the suppository to the subject.

In at least one example, the suppository provides a reduction in Mayo Endoscopic Score (Mayo ES) in the subject of at least 2 points in 30 days or less of starting once a day administration of the suppository to the subject.

In at least one example, the suppository provides a reduction in ulcerative colitis endoscopic index of severity (UCEIS) in the subject of at least 1 point in 8 weeks or less of starting once a day administration of the suppository to the subject.

In at least one example, the suppository provides a reduction in ulcerative colitis endoscopic index of severity (UCEIS) in the subject of at least 1 point in 6 weeks or less of starting once a day administration of the suppository to the subject.

In at least one example, the suppository provides a reduction in ulcerative colitis endoscopic index of severity (UCEIS) in the subject of at least 1 point in 30 days or less of starting once a day administration of the suppository to the subject.

In at least one example, the suppository provides a reduction in ulcerative colitis endoscopic index of severity (UCEIS) in the subject of at least 2 points in 8 weeks or less of starting once a day administration of the suppository to the subject.

In at least one example, the suppository provides a reduction in ulcerative colitis endoscopic index of severity (UCEIS) in the subject of at least 2 points in 6 weeks or less of starting once a day administration of the suppository to the subject.

In at least one example, the suppository provides a reduction in ulcerative colitis endoscopic index of severity (UCEIS) in the subject of at least 2 points in 30 days or less of starting once a day administration of the suppository to the subject.

In at least one example, an additional inflammatory bowel disease treatment is administered at the same time or over the same time period at the rectal suppository.

In at least one example, the additional inflammatory bowel disease treatment is selected from any one or more of 5-aminosalicylates (5-ASAs, for example mesalazine, olsalazine, balsazide, sulfasalazine), corticosteroids (for example prednisone), a biologic.

In at least one example, an additional treatment is administered for the symptoms of inflammatory bowel disease at the same time or over the same time period at the rectal suppository.

In at least one example, an additional treatment for the symptoms of inflammatory bowel disease is selected from a laxative, an antidiarrheal, pain relief.

In one aspect there is provided a method of manufacturing a rectal suppository, the method comprising the steps of:

(a) heating a hard fat to become a liquid hard fat,
(b) adding at least one surfactant to the liquid hard fat,
(c) adding 6-thioguanine to the liquid hard fat,
(d) forming the hard fat into a rectal suppository,
wherein step (b) is optionally carried out before step (c) or after step (c).

In at least one example, step (b) is carried out prior to step (c).

In at least one example, the hard fat is heated to about 40 to 90° C.

In at least one example, the hard fat is heated to about 40 to 80° C.

In at least one example, the hard fat is heated to about 40 to 70° C.

In at least one example, the hard fat is heated to about 40 to 65° C.

In at least one example, the hard fat is heated to about 40 to 60° C.

In at least one example, the hard fat is stirred or agitated while heated.

In at least one example, the hard fat is stirred using overhead stirring.

In at least one example, the method further comprises the step of adding at least one antioxidant to the liquid hard fat.

In at least one example, the at least one antioxidant is added to the liquid hard fat with the surfactant.

In at least one example, the 6-thioguanine is added to the liquid hard fat in a portion of liquid hard fat.

In at least one example, the portion of liquid hard fat is removed from the liquid hard fat after the addition of the at least one surfactant.

In at least one example, the portion of liquid hard fat is removed from the liquid hard fat after the addition of the at least one surfactant and at least one antioxidant.

In at least one example, the method further comprises homogenizing the liquid hard fat, surfactant, and 6-thioguanine.

In at least one example, the homogenizing comprises milling the liquid hard fat, surfactant, and 6-thioguanine.

In at least one example, the method further comprises reducing the particle size of the 6-thioguanine.

In at least one example, the particle size is reduced by milling the 6-thioguanine. In at least one example, the particle size is reduced by wet milling the 6-thioguanine.

In at least one example, the milling is carried out after the addition of the 6-thioguanine to the liquid hard fat.

In at least one example, the milling is ball milling.

In at least one example, the ball milling uses beads of about 0.1 to 2 mm. In at least one example, the ball milling uses beads of about 1 to 1.5 mm. In at least one example, the ball milling uses beads of about 1.2 to 1.4 mm.

In at least one example, the method further comprises the step of adding at least one suspending agent to the liquid hard fat.

In at least one example, the least one suspending agent is added to the liquid hard fat prior to the 6-thioguanine.

In at least one example, the least one suspending agent is added to the liquid hard fat prior after the surfactant.

In at least one example, the hard fat is formed into the suppository by transferring the liquid hard fat into a mold.

In at least one example, the hard fat is cooled to about 31 to 40° C. prior to transferring to the mold.

In at least one example, the hard fat is cooled to about 33 to 35° C. prior to transferring to the mold.

In at least one example, the hard fat is cooled to about 37 to 40° C. prior to transferring to the mold.

In at least one example, the had fat is cooled to about 15 to 25° C. after being transferred into the mold. In at least one example, the had fat is cooled to about 17 to 22° C. after being transferred into the mold.

For the avoidance of doubt, the embodiments and/or examples may apply alone or in any combination of two or more thereof to any one or more of the aspects set forth above where the context allows.

Further aspects of the present invention and further embodiments and/or examples of the aspects described in the preceding paragraphs will become apparent from the following description, given by way of example and with reference to the accompanying drawings.

BRIEF DESCRIPTION OF THE FIGURES

The invention will be described in conjunction with the following Figures in which like reference numerals designate like elements and wherein:

FIGS. 6A, 6B, and 6C are histograms of particle size distribution for different batches of thioguanine. FIG. 6D is a histogram of a placebo rectal suppository formulation containing silicon dioxide. FIG. 6E is a histogram of a milled rectal suppository formulation. FIG. 6F1 is a histogram of an unmilled rectal suppository formulation. FIG. 6F2 is a histogram of a milled rectal suppository formulation. The histograms show Volume Density (%) on the y-axis, ranging from 0 to 8 (with markers at 0, 2, 4, 6 and 8) and Size Classes (μm) on the x-axis ranging from 0.01 to 10,000.0 (with markers at 0.01, 0.1, 1.0, 10.0, 100.0, 1,000.0 and 10,000.0).

DEFINITION OF TERMS

Figure 1:
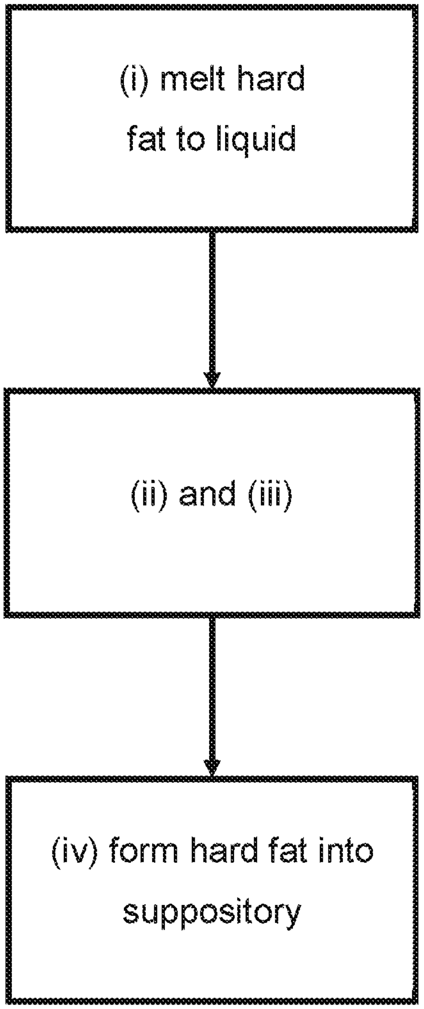
FIG. 1 is a schematic of a method of manufacturing a rectal suppository.

As used herein the term "active pharmaceutical ingredient" ("API") or "pharmaceutically active agent" or "active agent" or "active" is a drug or agent which can be employed as disclosed herein and is intended to be used in the human or animal body in order to heal, to alleviate, to prevent or to diagnose diseases, ailments, physical damage or pathological symptoms; allow the state, the condition or the functions of the body or mental states to be identified; to replace active substances produced by the human or animal body, or body fluids; to defend against, to eliminate or to render innocuous pathogens, parasites or exogenous substances or to influence the state, the condition or the functions of the body or mental states. 6-thioguanine is an example of an API.

An amount is "effective" as used herein, when the amount provides an effect in the subject. As used herein, the term "effective amount" or "therapeutically effective" means an amount of a compound or composition sufficient to significantly induce a positive benefit, including independently or in combinations the benefits disclosed herein, but low enough to avoid serious side effects, i.e., to provide a reasonable benefit to risk ratio, within the scope of sound judgment of the skilled artisan.

As used herein, the terms "prevent," "preventing" and "prevention" in the context of the administration of a therapy to a subject refer to the prevention or inhibition of the recurrence or onset of a disease or condition, such as inflammatory bowel disease, ulcerative colitis, Crohn's disease, ulcerative proctitis, proctosigmoiditis, and/or left-sided colitis, or a symptom thereof in a subject resulting from the administration of a therapy (e.g., a prophylactic or therapeutic agent), or a combination of therapies (e.g., a combination of prophylactic or therapeutic agents).

As used herein, the terms "treat," "treatment," and "treating" in the context of the administration of a therapy to a subject refer to the reduction or inhibition of the progression and/or duration of a disease or condition, such as such as inflammatory bowel disease, ulcerative colitis, Crohn's disease, ulcerative proctitis, proctosigmoiditis, and/or left-sided colitis, the reduction or amelioration of the severity of a disease or condition, such as such as inflammatory bowel disease, ulcerative colitis, Crohn's disease, ulcerative proctitis, proctosigmoiditis, and/or left-sided colitis, and/or the amelioration of one or more symptoms thereof resulting from the administration of one or more therapies.

As used herein, the terms "manage", "management" and "managing" in the context of the administration of a therapy to a subject refer to the prevention or inhibition of the development of a disease or condition, such as inflammatory bowel disease, ulcerative colitis, Crohn's disease, ulcerative proctitis, proctosigmoiditis, and/or left-sided colitis, or a symptom thereof in a subject resulting from the administration of a therapy (e.g., a prophylactic or therapeutic agent), or a combination of therapies (e.g., a combination of prophylactic or therapeutic agents).

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In at least one example, the subject is a non-human animal such as a farm animal (e.g., a horse, pig, or cow) or a pet (e.g., a dog or cat). In at least one example, the subject is an elderly human. In at least one example, the subject is a human adult. In at least one example, the subject is a human child. In at least one example, the subject is a human infant.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "about" when used in conjunction with a stated numerical value or range has the meaning reasonably ascribed to it by a person skilled in the art, i.e. denoting somewhat more or somewhat less than the stated value or range, for example it may vary by as much as 10% or even as much as 9%, 8%, 7%, 6%, 5%, 4%, 3%, 2%, 1%, to the stated numerical value or range.

As used herein, except where the context requires otherwise, the term "comprise" and variations of the term, such as "comprising", "comprises" and "comprised", are not intended to exclude further additives, components, integers or steps.

As used herein, the term "hard fat" means one or more glyceride(s) of one or more saturated fatty acid(s), alternatively one or more glyceride(s) of one or more saturated fatty acid(s) which is substantially solid at room temperature (for example about 20° C.), alternatively one or more mono-, di- and/or triglyceride esters of one or more C10 to C18 saturated fatty acid(s) which is substantially solid at room temperature (for example about 20° C.), alternatively one or more mono-, di- and/or triglyceride esters of one or more C10 to C18 saturated fatty acid(s) which is substantially solid at room temperature (for example about 20° C.) comprising less than about 10% of one or more unsaturated fatty acid(s), or less than about 5% of one or more unsaturated fatty acid(s), or less than about 2% of one or more unsaturated fatty acid(s), or less than about 1% of one or more unsaturated fatty acid(s). The % of unsaturation is based on mole percent. There may be one or more of mono-, di- or triglyceride esters of a fatty acid(s) and/or one or more fatty acid(s) (for example one or more chain lengths of fatty acid(s)) forming the ester (for example one or more chain lengths selected from C10 to C18). Reference to "hard fat" should not be taken to include cocoa butter.

As used herein, reference to testing for dissolution or release of 6-thioguanine in vitro may be tested using the conditions: apparatus I (basket, 40 mesh) at speed 100 rpm±4 rpm, in 900 mL per vessel of dissolution medium 0.05 M phosphate buffer, pH 6.8±0.05, at 37.0° C.±0.5° C.

As used herein, the term "rectal suppository" means a dosage form which is formulated to be administered rectally, i.e. a rectal suppository is a suitable shape and/or size to be administered rectally and includes at least a suitable pharmaceutically acceptable excipient(s). Suitable pharmaceutically acceptable excipient(s) either melt at body temperature or are water-soluble and/or water-miscible to be capable of dispersion in rectal fluids, and are capable of delivering an API to the rectal area. Suitable pharmaceutically acceptable excipients are preferably substantially nontoxic and/or non-irritating to mucous membranes.

DETAILED DESCRIPTION

Described herein is a rectal suppository comprising 6-thioguanine, at least one hard fat, and at least one surfactant.

Further or alternatively, described herein is a rectal suppository comprising 6-thioguanine, at least one hard fat, at least one surfactant, optionally at least one suspending agent, and optionally at least one antioxidant.

Further or alternatively, described herein is a method of preventing, treating and/or managing inflammatory bowel disease, the method comprising administering a rectal suppository as described herein to a subject in need thereof.

Further or alternatively, described herein is a method of preventing, treating and/or managing inflammatory bowel disease, the method comprising administering a rectal suppository comprising 6-thioguanine, at least one hard fat, and at least one surfactant.

Further or alternatively, described herein is a method of preventing, treating and/or managing inflammatory bowel disease, the method comprising administering a rectal suppository comprising 6-thioguanine, at least one hard fat, at least one surfactant, optionally at least one suspending agent, and optionally at least one antioxidant.

Further or alternatively, described herein is use of a rectal suppository comprising 6-thioguanine as described herein in the manufacture of a medicament for prevention, treatment and/or management of inflammatory bowel disease.

Further or alternatively, described herein is use of a rectal suppository comprising 6-thioguanine, at least one hard fat, and at least one surfactant, in the manufacture of a medicament for prevention, treatment and/or management of inflammatory bowel disease.

Further or alternatively, described herein is use of a rectal suppository comprising 6-thioguanine, at least one hard fat, at least one surfactant, optionally at least one suspending agent, and optionally at least one antioxidant, in the manufacture of a medicament for prevention, treatment and/or management of inflammatory bowel disease.

Further or alternatively, described herein is a rectal suppository comprising 6-thioguanine as described herein for prevention, treatment and/or management of inflammatory bowel disease.

Further or alternatively, described herein is a rectal suppository comprising 6-thioguanine, at least one hard fat, and at least one surfactant, for prevention, treatment and/or management of inflammatory bowel disease.

Further or alternatively, described herein is a rectal suppository comprising 6-thioguanine, at least one hard fat, at least one surfactant, optionally at least one suspending agent, and optionally at least one antioxidant, for prevention, treatment and/or management of inflammatory bowel disease.

Further or alternatively, described herein is use of a rectal suppository comprising 6-thioguanine as described herein for prevention, treatment and/or management of inflammatory bowel disease.

Further or alternatively, described herein is use of a rectal suppository comprising 6-thioguanine, at least one hard fat, and at least one surfactant, for prevention, treatment and/or management of inflammatory bowel disease.

Further or alternatively, described herein is use of a rectal suppository comprising 6-thioguanine, at least one hard fat, at least one surfactant, optionally at least one suspending agent, and optionally at least one antioxidant, for prevention, treatment and/or management of inflammatory bowel disease.

Further or alternatively, described herein is a rectal suppository comprising about 1 to 9 mg of 6-thioguanine.

Further or alternatively, described herein is a rectal suppository comprising about 1 to 9 mg of 6-thioguanine and at least one hard fat.

Further or alternatively, described herein is a rectal suppository comprising about 1 to 9 mg of 6-thioguanine and a pharmaceutically acceptable excipient.

Further or alternatively, described herein is a rectal suppository comprising about 1 to 9 mg of 6-thioguanine, at least one hard fat, and at least one surfactant.

Further or alternatively, described herein is a rectal suppository comprising about 1 to 9 mg of 6-thioguanine, at least one hard fat, and at least one surfactant, optionally at least one suspending agent, and optionally at least one antioxidant.

Further or alternatively, described herein is a method of preventing, treating and/or managing inflammatory bowel disease in a subject, the method comprising rectally administering to a subject about 1 to 9 mg 6-thioguanine in the form of a rectal suppository.

Further or alternatively, described herein is use of a rectal suppository comprising 6-thioguanine in the manufacture of a medicament for prevention, treatment and/or management of inflammatory bowel disease, wherein the suppository comprises about 1 to 9 mg 6-thioguanine.

Further or alternatively, described herein is a rectal suppository comprising 6-thioguanine for prevention, treatment and/or management of inflammatory bowel disease, wherein the suppository comprises about 1 to 9 mg 6-thioguanine.

Further or alternatively, described herein is use of a rectal suppository comprising 6-thioguanine for prevention, treatment and/or management of inflammatory bowel disease, wherein the suppository comprises about 1 to 9 mg 6-thioguanine.

Further or alternatively, described herein is a method of manufacturing a rectal suppository, the method comprising the steps of (a) heating a hard fat to become a liquid hard fat, (b) adding at least one surfactant to the liquid hard fat, (c) adding 6-thioguanine to the liquid hard fat, (d) forming the hard fat into a rectal suppository, wherein step (b) is optionally carried out before step (c) or after step (c).

6-Thioguanine

The structure of 6-thioguanine (thioguanine, 6-TG, 2-amino-1H-purine-6(7H)-thione) is shown below:

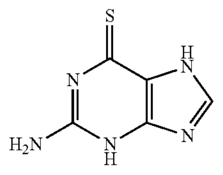 [SMILES: Nc1nc(=S)c2[nH]cnc2[nH]1]

As will be apparent to those skilled in the art, the 6-TG may be available and/or used as a hydrate (for example heptahydrate or hemihydrate) or a salt. When considering the amount, percentage or ratio of the 6-thioguanine. in the pharmaceutical composition the mass of the water in a hydrate or salt should not be included.

6-Thioguanine is a member of the thiopurine family of medicines. The thiopurines are prodrugs which are converted to the active metabolites thioguanine nucleotides (6-TGNs) in the body. The principal 6-TGN is 6-thioguanosine-triphosphate (6-TGTP), and to a lesser extent 6-TGMP or 6-TGDP. Other members of the thiopurine family are 6-mercaptopurine (6-MP) and azathiopurine (AZA). However, 6-MP and AZA are believed to have different metabolic pathways to 6-TG. It is believed 6-MP and AZA are converted by some cells in the body (including liver cells and white blood cells) to the 6-TGN. This conversion pathway is rate limited by the enzyme inosine monophosphate dehydrogenase (IMPDH), such that the 6-TGNs take days to appear, a steady state takes weeks to reach, and clinical action takes months. By contrast 6-thioguanine is believed to have a more direct metabolic pathway to 6-TGTP via metabolism by the enzyme hypoxanthine-guanine phosphoribosyltransferase (HPRT). This can provide faster clinical action but can also lead to serious hepatotoxic side-effects producing liver vascular disease such as sinusoidal obstructive syndrome (SOS), veno-occlusive disease (VOD), or nodular regenerative hyperplasia (NRH). These side-effects are not significantly associated with 6-MP or AZA.

WO2017/054042 (also published as US2016/15764247) described the finding that mice lacking in the key enzyme HPRT still showed rapid and appreciable reduction in induced colitis on treatment with 6-thioguanine despite lacking the conventional metabolic route to convert 6-thioguanine to the active metabolite in the liver and leukocytes. It was believed that 6-thioguanine was converted to 6-TGTP via HPRT in resident intestinal bacteria and/or diseased mucosa or epithelial and resident white cells at a site of inflammation. It was therefore believed 6-thioguanine could act locally without appreciable systemic concentration.

The rectal suppository may comprise a single thiopurine or purine analog compound. It is believed only the thiopurine 6-thiogunanine acts topically at the site of administration.

The rectal suppository comprises a therapeutically effective amount of 6-thioguanine.

The rectal suppository may comprise about 1 to 30 mg, or about 3 to 25 mg, or about 5 to 20 mg of 6-thioguanine in each suppository.

Alternatively, the rectal suppository may comprise about 8 to 30 mg, or about 8 to 25 mg, or about 10 to 20 mg of 6-thioguanine in each suppository. Alternatively, the rectal suppository may comprise about 15 to 30 mg, or about 17 to 25 mg, or about 20 mg of 6-thioguanine in each suppository.

Alternatively, the rectal suppository may comprise about 6 to 15, or about 8 to 12 mg, or about 10 mg of 6-thioguanine in each suppository.

Alternatively, the rectal suppository may comprise about 1 to 9 mg, or about 2 to 9 mg, or about 3 to 9 mg, or about 3 to 7 mg, or about 4 to 6 mg, or about 5 mg of 6-thioguanine in each suppository.

A lower dose of 6-thioguanine in the rectal suppository, and/or low systemic levels of 6-thioguanine (and/or metabolites), while still being therapeutically effective, is beneficial due to the known toxicity of 6-thioguanine at higher levels.

The rectal suppository formulation may comprise about 0.05 to 5% w/w, or about 0.05 to 3% w/w, or about 0.05 to 2.5% w/w. or about 0.05 to 2% w/w, or about 0.2 to 1.5% w/w, or about 0.3 to 1.1% w/w of 6-thioguanine.

Alternatively, the rectal suppository formulation may comprise about 0.4 to 2% w/w, or about 0.4 to 1.5% w/w, or about 0.5 to 1.1% w/w of 6-thioguanine.

Alternatively, the rectal suppository formulation may comprise about 0.6 to 2% w/w, or, about 0.7 to 1.5% w/w, or about 0.8 to 1.1% w/w, or about 1.1% w/w of 6-thioguanine.

Alternatively, the rectal suppository formulation may comprise about 0.4 to 1.0% w/w, or about 0.4 to 0.9% w/w, or about 0.4 to 0.8% w/w, or about 0.5% w/w of 6-thioguanine.

Alternatively, the rectal suppository formulation may comprise about 0.05 to 0.4% w/w, or about 0.1 to 0.4% w/w, or about 0.2 to 0.4% w/w of 6-thioguanine, or about 0.3% w/w of 6-thioguanine.

The 6-thioguanine may be substantially suspended in the hard fat, for example the 6-thioguanine is substantially insoluble in the hard fat.

There is a wide range of techniques that may be utilized to characterize the particle size of a material. Those skilled in the art also understand that almost all these techniques do not physically measure the actual particle size, as one might measure something with a ruler, but measure a physical phenomenon which is interpreted to indicate a particle size.

For measurements made using a laser diffraction instrument, or an equivalent method known in the art, the term "median particle size" is defined as the median particle diameter as determined on an equivalent spherical particle volume basis. Where the term median is used, it is understood to describe the particle size that divides the population in half such that 50% of the population is greater than or less than this size. The median particle size is often written as D50, D(0.50), D[v,0.5], or D[0.5] or similar. As used herein D50, D[v,0.5], D(0.50) or D[0.5] or similar shall be taken to mean 'median particle size'.

The term "Dx of the particle size distribution" (or similar) refers to the xth percentile of the distribution; thus, D90 refers to the $90^{th}$ percentile, D95 refers to the $95^{th}$ percentile, and so forth. Taking D90 as an example this may be written as, D[v,0.9], D(0.90) or D[0.9] or similar. With respect to the median particle size and Dx an upper-case D or lowercase d are interchangeable and have the same meaning.

Particle size distribution, for example of an API and/or other component of the formulation, may be described by the distribution volume at various percentage of the volume, for example at 10%, 50%, and 90% of the volume.

A commonly used way of describing a particle size distribution measured by laser diffraction, or an equivalent method known in the art, is to describe what % of a distribution is under or over a nominated size. The term "percentage less than" also written as "%<" is defined as the percentage, by volume, of a particle size distribution under a nominated size—for example the %<1000 nm. The term "percentage greater than" also written as "%>" is defined as the percentage, by volume, of a particle size distribution over a nominated size—for example the %>1000 nm.

The 6-thioguanine in the rectal suppository may have a D50 particle size distribution of less than about 100 μm, or less than about 80 μm, or less than about 60 μm, or less than about 40 μm, or less than about 30 μm, or less than about 20.

The 6-thioguanine in the rectal suppository may have a D50 particle size distribution of about 1 to 100 μm, or about 1 to 80 μm, or about 1 to 60 μm, or about 1 to 40 μm, or about 1 to 30 μm, or about 1 to 20 μm.

In particular, the suppository formulation may be milled during manufacturing. In such cases the 6-thioguanine in the rectal suppository may have a D50 particle size distribution of less than about 50 μm, or 40 μm, or less than about 30 μm, or less than about 20 μm, or the 6-thioguanine in the rectal suppository may have a particle size distribution of D50 of about 1 to 50 μm, or about 1 to 40 μm, or about 1 to 30 μm, or about 1 to 20 μm.

The rectal suppository may have a D50 particle size distribution (of all particles in the suppository) of less than about 50 μm, or less than about 40 μm, or less than about 30 μm, or less than about 25 μm, or the rectal suppository may have a D50 particle size distribution of about 1 to 50 μm, or about 1 to 40 μm, or about 1 to 30 μm, or about 10 to 30 μm. The rectal suppository may have a D50 particle size distribution of about 1 to 40 μm.

Hard fat

Pharmaceutically acceptable hard fats are commercially available. The reference to "hard" in the name is in relation to the physical state at room temperature (for example 20° C.). However, hard fats are designed to melt at 33 to 39° C. The melting range varies between hard fats. Examples are shown in Table 1.

The hard fats are generally synthetically produced, for example, in the Suppocire range of hard fats available from Gattefossé the products without prefix "N" are made by interesterification of hydrogenated palm oil and hydrogenated palm kernel oil. The prefix 'N' indicates hard fats which are made by direct esterification between fatty acids and glycerol. "M" indicates a low hydroxyl value (<15). The Suppocire range provides a range of fats with different melting points/ranges, for example from low 32.5° C. to high >40° C. The letters in the range indicate melting point/range, for example Al<A<B<C<D.

The Witepsol range of hard fats from IOI Oleochemical comprises glycerol esters of vegetable saturated fatty acids, mainly lauric acid. Starting materials are purified coconut and palm kernel oils. After preliminary purification, the oils are cleaved into their fatty acids and glycerol by means of water at high pressure and acidic or alkaline catalysts. The fatty acid mixture is subjected to catalytic hydrogenation and subsequently to fractional vacuum distillation, and the low molecular weight caproic, caprylic, and capric acids (C6-C10) are removed. The C12-C18 fatty acids are adjusted to the correct mixture for the hard fat grade and esterified with glycerol. The fatty acid spectrum, the stoichiometry of the reaction mixture, and the reaction times and temperatures determine the properties of the product, such as melting range, solid fat index, hardness, mono-, di-, triglyceride content (emulsifiability/dispersibility) and viscosity.

Some commercial hard fats also include additives to modify the viscosity or consistency (such as bees wax).

For comparison, cocoa butter (theobroma oil) is also considered an oleaginous base used in rectal suppositories. However, cocoa butter is composed of mixture of triglycerides, predominantly made up of the fatty acids oleic acid (C18:1), palmitic acid (C16:0) and stearic acid (C18:0). It is a natural product, so the composition varies, but may have a saturated fatty acid content of about 57-64% and an unsaturated fatty acid content of about 36-43%. Cocoa butter has a melting range of about 30 to 35° C., but is a polymorphic compound, so the melting point can change to about 25 to 30° C. if heated above 35° C.

TABLE 1

Examples of commercially available hard fats

| Hard Fat | Description | Hydroxyl value (mg KOH/g) | Melting range-capillary tube (° C.) |
|---|---|---|---|
| Gattefossé Suppocire A | Consists of mono-, di- and triglyceride esters of fatty acids (C10 to C18), the triester fraction being predominant | 20-30 | 34-38 |
| Gattefossé Suppocire AM | Consists of mono-, di- and triglyceride esters of fatty acids (C10 to C18), the triester fraction being predominant | <10 | 34-36 |
| Gattefossé Suppocire AML | Consists of mono-, di- and triglyceride esters of fatty acids (C10 to C18), the triester fraction being predominant. Contains lecithin. | <10 | 34-38 |
| Gattefossé Suppocire BM | Consists of mono-, di- and triglyceride esters of fatty acids (C10 to C18), the triester fraction being predominant | <10 | 35-39 |
| Gattefossé Suppocire NB | Consists of mono-, di- and triglyceride esters of fatty acids (C10 to C18), the triester fraction being predominant | 20-30 | 35-39 |
| Gattefossé Suppocire NAS 50 | Consists of mono-, di- and triglyceride esters of fatty acids (C10 to C18), the triester fraction being predominant. Includes modified monoglyceride content providing hydrophilic properties. | 40-50 | 33.5-35.5 |
| Gattefossé Suppocire NA15 | Consists of mono-, di- and triglyceride esters of fatty acids (C10 to C18), the triester fraction being predominant | 5-15 | 33.5-35.5 |
| BASF Novata B PH | Mixture of triglycerides, diglycerides and monoglycerides. | 20-30 | 33.5-35.5 |

The rectal suppository may comprise about 80 to 99.9% w/w hard fat, or about 85 to 99.5% w/w hard fat, or about 90 to 99.5% w/w hard fat, or about 95 to 99.5% w/w hard fat, or about 80 to 99% w/w hard fat, or about 85 to 99% w/w hard fat, or about 90 to 99% w/w hard fat, or about 95 to 99% w/w hard fat.

The rectal suppository formulation may comprise hard fat comprising mono-, di- and/or triglyceride esters of C10 to C18 fatty acids. The hard fat may comprise mono-, di- and triglyceride esters of C10 to C18 fatty acids. The triglyceride esters may be predominant.

The rectal suppository may comprise triglyceride esters made by interesterification of hydrogenated palm oil and hydrogenated palm kernel oil.

The rectal suppository may comprise hard fat with a hydroxyl value of less than 40 mg KOH/g, or a hydroxyl value of about 1 to 35 mg KOH/g, or a hydroxyl value of about 1 to 30 mg KOH/g. It is believed hard fats with higher hydroxyl may be less chemically stable, for example more prone to oxidation. The rectal suppository may have a melting range of about 34 to 38° C., or a melting range of about 34 to 36° C. (for example, at 1 atmosphere of pressure).

Alternative Suppository Bases

The rectal suppository comprises at least one suitable pharmaceutically acceptable excipient(s) which either melt at body temperature (for example an oleaginous base, such as a hard fat or cocoa butter/theobroma oil, emulsified theobroma oil) or are water-soluble and/or water-miscible to be capable of dispersion in rectal fluids (for example a hydrophilic base, such as one or a mixtures of polyethylene glycol(s) (PEGs) of various molecular weights, and/or fatty acid esters of polyethylene glycol), which are capable of delivering an API to the rectal area.

The rectal suppository may comprise about 1 to 9 mg of 6-thioguanine and a pharmaceutically acceptable excipient, selected from an oleaginous base and a hydrophilic base.

Surfactant

Examples of commercially available surfactants and their hydrophilic-lipophilic balance (HLB) values are shown in Table 2. Hydrophilic-lipophilic balance (HLB) is the weight percentage of the hydrophilic groups to the hydrophobic groups in a molecule. The most commonly used HLB scale has values ranging from 1-20, however, in some cases the scale goes higher (for example from 1-40) to accommodate outliers such as sodium lauryl sulfate (SLS) with a HLB value of approximately 40.

TABLE 2

Examples of surfactants

| Surfactant names | Approximate HLB value of surfactant |
|---|---|
| Sodium lauryl sulfate (SLS) | 40 |
| Potassium oleate | 20 |

TABLE 2-continued

| Examples of surfactants | |
|---|---|
| Surfactant names | Approximate HLB value of surfactant |
| Polyoxyethylene (100) stearate | 19 |
| Sodium oleate | 18 |
| Sucrose palmitate | 16 |
| Sucrose stearate | 11-15 |
| Tween 80 (polysorbate 80, polyoxyethylene sorbitan monooleate, | 15 |
| Tween 65 (polysorbate 65, polyoxyethylene-20-sorbitan tristearate, PEG-20 sorbitan tristearate) | 11 |
| Tween 60 (polysorbate 60, polyoxyethylene-60 sorbitan monostearate) | 15 |
| Tween 40 (polysorbate 40, polyoxyethylene sorbitan monopalmitate) | 16 |
| Tween 20 (polysorbate 20, polyoxyethylene sorbitan monolaurate, PEG(20)sorbitan monolaurate) | 17 |
| Brij S20 (Polyethylene glycol octadecyl ether, Polyoxyethylene (20) stearyl ether) | 15 |
| Brij ™ CS12 (PEG 12 cetostearyl ether) | 13 |
| Brij ™ S10 (polyethylene glycol octadecyl ether, polyoxyethylene (10) stearyl ether) | 12 |
| Brij ™ L9 (polidocanol, PEG-9 lauryl alcohol, hydroxyl polyethoxy dodecane) | 14 |
| Cremophor ® EL (Castor oil polyoxyethylene ether, Ethoxylated castor oil, PEG-35 castor oil, Polyoxyl 35 castor oil, polyoxyl 35 castor oil) | 12-14 |
| Gelucire 48/16 (polyoxyl-32 stearate, PEG-32 (MW 1500) esters of palmitic (C16) and stearic (C18) acids) | 12 |
| Gelucire 50/13 (stearoyl polyoxyl-32 glycerides, mono, di- and triglycerides and PEG-32 (MW 1500) mono- and diesters of palmitic (C16) and stearic (C18) acids) | 11 |
| SPAN 120 (sorbitan isostearate) | 5 |
| SPAN 83 (sorbitan sesquioleate) | 4 |
| SPAN 80 (sorbitan monooleate) | 4 |
| SPAN 60 (sorbitan monostearate) | 5 |
| SPAN 65 (sorbitan tristearate) | 2 |
| SPAN 40 (sorbitan monopalmitate) | 7 |
| SPAN 20 (sorbitan monolaurate) | 9 |
| Lecithin | 3-5 |

As shown in Examples 2 and/or 5, the surfactant increases the rate and/or amount of dissolution under in vitro dissolution testing. In vitro dissolution testing may provide an indication of in vivo performance with respect to diffusion and dissolution of the 6-TG from the rectal suppository.

The rectal suppository may comprise a non-ionic surfactant.

The rectal suppository may comprise a surfactant with a hydrophilic-lipophilic balance (HLB) of equal to or greater than about 10.

The rectal suppository may comprise suitable surfactants, by way of example and without limitation, including, polysorbates, polyoxyethylene derivatives of natural or hydrogenated vegetable oils (such as castor oil), alkyl/dialykyl sulfate, sulfonate or sulfosuccinate salts, polyoxyethylene fatty acid esters, phospholipids, transesterification products of natural vegetable oil triglycerides and polyalkylene polyols, sorbitan fatty acid esters, pentaerythritol fatty acid esters, polyoxyethylene glycol alkyl ethers and/or esters; sucrose esters, ethoxylated fatty alcohols, fatty acid salts and the like, and mixtures thereof.

Examples of polysorbates (e.g. polyoxyethylene-sorbitan fatty acid ester, for example mono-, di- and trilauryl, palmityl, stearyl and oleyl esters) include polysorbate 80, polysorbate 65, polysorbate 60, polysorbate 40, polysorbate 20.

An Example of a polyoxyethylene derivatives of natural or hydrogenated vegetable oils (such as castor oil) is polyoxyl 35 castor oil.

Examples of alkyl/dialykyl sulfate, sulfonate or sulfosuccinate salts include sodium lauryl sulfate, dioctyl sodium sulfosuccinate and disodium laureth sulfosuccinate.

An example of a polyoxyethylene fatty acid ester is PEG 100 stearate.

An example of a phospholipid is lecithin.

Examples of sorbitan fatty acid esters include sorbitan isostearate, sorbitan sesquioleate, sorbitan monooleate, sorbitan monostearate, sorbitan tristearate, sorbitan monopalmitate, sorbitan monolaurate.

Examples of polyoxyethylene glycol alkyl ethers and/or esters include polyethylene glycol octadecyl ether, polyethylene glycol 12 cetostearyl ether.

Examples of sucrose esters (for example sucrose fatty esters) include sucrose palmitate and sucrose stearate.

Examples of fatty acid salts (for example oleic acid) include potassium oleate and sodium oleate.

Examples of specific surfactants which may be used include, without limitation, polyoxyethylene castor oil derivatives, such as polyoxyethylene glycerol triricinoleate polyoxyl 35 castor oil (for example CREMOPHOR® EL, available from BASF Corporation), and polyoxyl 40 hydrogenated castor oil (for example CREMOPHOR® RH40, available from BASF Corporation); mono-fatty acid esters of polyoxyethylene (20) sorbitan (such as polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene (20) sorbitan monolaurate (TWEEN® 20); polyoxyethylene glycol alkyl ethers and esters (such as polyethylene glycol octadecyl ether (Brij S20, polyoxyethylene (20) stearyl ether)) and mixtures thereof.

The rectal suppository may comprise polysorbate 80.

The surfactant may be liquid at room temperature (for example about 20° C. and 1 atmosphere of pressure) and/or may have a melting point below 35° C. (for example, at 1 atmosphere of pressure).

The rectal suppository may comprise about 0.1 to 20% w/w, or about 0.1 to 15% w/w, or about 0.1 to 10% w/w, or about 0.1 to 5% w/w, about 0.1 to 5% w/w, or about 0.2 to 3% w/w, or about 0.4 to 3% w/w, or about 0.5 to 3% w/w, or about 0.5 to 2% w/w surfactant.

The rectal suppository may comprise about 0.1 to 5% w/w, or about 0.2 to 3% w/w, or about 0.4 to 3%, or about 0.5 to 3% w/w, or about 0.5 to 2% w/w, or about 0.5 to 1.5% w/w polysorbate 80.

Suspending Agent

The rectal suppository may comprise a suspending agent.

A suspending agent may improve the uniformity of the rectal suppositories within a batch, for example, reduce the difference between the amount of 6-thiogunanine in each suppository in a batch and/or reduce the standard deviation of the amount of 6-thioguanine in each suppository in a batch. A suspending agent may modify the viscosity of the rectal suppository formulation to provide the suspending effect. The suspending agent may in such cases alternatively be called a viscosity modifier.

As shown in Example 3, the addition of a suspending agent improved the uniformity of the amount of 6-thioguanine in each unit/suppository across a batch of units/suppositories made from a rectal suppository formulation.

The rectal suppository may comprise about 0.05 to 10% w/w, or about 0.1 to 5% w/w, or about 0.1 to 4% w/w, or about 0.1 to 3% w/w, or about 0.1 to 2% w/w, or about 0.1 to 1% w/w suspending agent.

The rectal suppository may comprise a suspending agent selected from one or more of silicon dioxide, a clay (including purified and/or refined clays), aluminum monostearate and magnesium stearate. The clay may be selected from one or more of kaolin, palygorskite, smectites, sylvite, bentonite, halite, and magnesium aluminum silicate.

The suspending agent may comprise silicon dioxide. The silicon dioxide may be fumed silica and/or colloidal silica. Examples of commercially available silica (silicon dioxide) based suspending agents include the range Aerosil® from Evonik.

The rectal suppository may comprise about 0.05 to 10% w/w, or about 0.1 to 5% w/w, or about 0.1 to 4% w/w, or about 0.1 to 3% w/w, or about 0.1 to 2% w/w, or about 0.1 to 1% w/w silicon dioxide.

Alternative or additional methods of improving and/or controlling the uniformity of the rectal suppositories within a batch may include control of the temperature of the liquid hard fat (for example controlling the viscosity of the hard fat) and/or control of agitation of the liquid hard fat and/or other methods.

Other Excipients

Hard fats may oxidize over time. The rectal suppository may comprise an antioxidant to ameliorate oxidation of the hard fat and/or other ingredients. Examples of suitable antioxidants may include one or more of butylated hydroxyanisole (BHA), butylated hydroxytoluene (BHT), propyl gallate, a tocopherol (e.g., α-tocopherol (vitamin E)), propionic acid, sodium nitrate, sodium nitrite, an anthocyanin, citric acid (for example citric acid monohydrate). The rectal suppository may comprise butylated hydroxyanisole (BHA) and/or vitamin E.

The antioxidant may be present in the rectal suppository in a range of about 0.0003 to 8%, or about 0.003 to 4% w/w, or about 0.003 to 2.5% w/w.

Treatment

The rectal suppository may be suitable for preventing, treating and/or managing inflammatory bowel disease a subject in need thereof. The inflammatory bowel disease preferably effects the rectum.

The inflammatory bowel disease may be ulcerative colitis or Crohn's disease, effecting the rectum. For example, the ulcerative colitis may be ulcerative proctitis, proctosigmoiditis, and/or left-sided colitis.

The rectal suppository may be administered, or formulated to be administered, once daily or twice daily.

The rectal suppository is suitable for rectal delivery, for example of a suitable size and/or shape for administration and/or retention. Compared to enemas, rectal suppositories are generally easier for patients to administer and retain, which may lead to greater compliance with treatment and preference by patients. Rectal suppositories may be in contact with a smaller and/or lower area of the digestive tract compared to enemas, which may make them particularly suited to treatment of ulcerative proctitis. Suppositories are generally more concentrated than enemas, for example in volume, so a greater concentration of active (for example 6-thioguanine) may be delivered to a localized area (for example the rectum). A rectal suppository may provide a lower level of 6-TGN in RBC, compared to an enema of the same dose, which may provide for lower toxicity.

The rectal suppository may have a total weight of about 800 to 3000 mg, or about 1000 to 3000 mg, or about 1200 to 3000 mg, or about 1500 to 3000 mg, or about 1800 to 2200 mg, or about 1800 to 2000 mg, or about 1000 to 2500 mg, or about 1000 to 2000 mg.

The rectal suppository may be substantially cylinder shaped preferably with at least one rounded end. Alternatively, the rectal suppository may be torpedo, oval (including an elongated oval), or conical (including frustoconical) shaped.

The rectal suppository provides a unit dose. The dose cannot be split, or multiple doses administered at once. The dose provided to the subject is therefore based on the amount of 6-thioguanine in the rectal suppository. The dose of rectal suppository used may be selected based on the body weight of a subject, or for a population, based on the weight range of the population. For example, the dose may be selected based on a weight range of 60 to 80 kg, however, the weight range used may vary by region.

The rectal suppository may provide a dose (for example a daily dose) of 6-thioguanine of about 0.01 to 0.4 mg per kg of body weight or a dose (for example a daily dose) of 6-thioguanine of about 0.1 to 0.4 mg per kg of body weight.

The method of preventing, treating and/or managing inflammatory bowel disease in a subject, may comprise rectally administering a suppository to a subject comprising as little as about 1 to 9 mg 6-thioguanine. Previous, oral dosing of 6-thioguaine has been in 40 mg tablets (about 2 mg/kg of body weight per day) to treat acute nonlymphocytic leukemias, or 10 mg or 20 mg tablets (0.3 mg per kg of body weight per day) to treat Crohn's disease or ulcerative colitis. There are no registered 6-thioguaine rectally administered products, however, previous trials have dosed at 20 mg per rectal dose (enema or suppository) (about 0.25-0.33 mg per kg of body weight)—see for example Crouwel F, Simsek M, van Doorn A S, Mulder C J J, Buiter H J C, Barclay M L, Florin T H, de Boer N K. "Rectally Administrated Thioguanine for Distal Ulcerative Colitis: A Multicenter Case Series", Inflammatory Bowel Diseases, Volume 29, Issue 6, June 2023, pages 1000-1004). It is therefore surprising such a low rectal suppository dose of about 1 to 9 mg 6-thioguanine is therapeutically effective.

The rectal suppository may provide a daily dose of 6-thioguanine of as little as about 0.01 to 0.1 mg per kg of body weight, or about 0.01 to 0.09 mg per kg of body weight, about 0.02 to 0.08 mg per kg of body weight, or about 0.03 to 0.08 mg per kg of body weight, or about 0.04 to 0.08 mg per kg of body weight, or about 0.05 to 0.08 mg per kg of body weight.

While reference is made to a "daily" "twice daily" dose, or "one a day" or "twice a day" dose, this refers to the number times the rectal suppository is administered in a day, it will be appreciated by those skilled in the art that the rectal suppository may not be administered every day, for example the rectal suppository may be administered every 2, 3, 4, 5, 6, or 7 days (or otherwise). For example, a rectal suppository may not be required every day, particularly, when being used as a maintenance dose.

An additional inflammatory bowel disease treatment, or treatment for the symptoms of inflammatory bowel disease may be administered at the same time or over the same time period at the rectal suppository. An example of treatment at the same time may be within an hour of administering the rectal suppository. An example, of the same time period may be, where a suppository is administered once daily, twice daily or every two days for a week, the additional treatment is administered in the same week. Examples of additional inflammatory bowel disease treatment include 5-aminosalicylates (5-ASAs), (for example mesalazine, olsalazine, balsazide, sulfasalazine), a corticosteroid (for example, prednisone) and/or a biologic. Examples of treatment for the symptoms of inflammatory bowel disease include a laxative, an antidiarrheal, pain relief. Inflammatory bowel disease is commonly associated with diarrhea, however, particularly during treatment, constipation can become an issue.

The rectal suppository may provide mean 6-TGN levels of less than about 150 pmol/8×$10^8$ RBC, or less than about 100 pmol/8×$10^8$ RBC, or less than about 75 pmol/8×$10^8$ RBC, or less than about 60 pmol/8×$10^8$ RBC, or less than about 30 pmol/8×$10^8$ RBC, or less than about 25 pmol/8×$10^8$ RBC, or less than about 20 pmol/8×$10^8$ RBC, 6 hours after administration of the suppository. However, lower 6-TGN levels in RBC are preferred while still remaining therapeutically effective. In particular, for the rectal suppository comprising about 1 to 9 mg of 6-thioguanine, the rectal suppository may provide mean 6-TGN levels of less than about 30 pmol/8×$10^8$ RBC, or less than about 25 pmol/8×$10^8$ RBC, or less than about 20 pmol/8×$10^8$ RBC, 6 hours after administration of the suppository. 6-TGN levels greater than 450 pmol/8×$10^8$ RBCs are associated with a higher risk of leukopenia and myelotoxicity (Afrasyab Khan, Arvenia B Berahmana, Andrew S Day, Murray L Barclay, Michael Schultz, New Zealand Medical Association Journal (NZMJ) 8 Mar. 2019, Vol 132 No 1491, ISSN 1175-8716).

The 6-TGN or 6-TG levels may be measured once the subject is at steady state, for example the subject has had a once-daily dose of the suppository for at least 2 weeks, or at least 4 weeks. "Steady state" is when drug concentrations consistently stay within therapeutic limits for long periods. The concentration around which the drug concentration consistently stays is known as the "steady-state concentration".

The rectal suppository may be considered safe to use while breast feeding. The rectal suppository may provide low 6-TGN and/or 6-TG levels in breast milk in the subject while the suppository is administered once a day to the subject, for example, at or below 15 ng/mL, at or below 10 ng/ml, at or below 5 ng/ml, at or below 2.5 ng/ml. The breast milk 6-TGN and/or 6-TG levels may be measured when the suppository is administered once a day to the subject for at least 28 days. The breast milk 6-TGN levels may be measured at 2, 6, or 9 hours after administration of the rectal suppository. In particular, the rectal suppository may comprise about 1 to 9 mg of 6-thioguanine, or about 5 mg.

The rectal suppository may provide a clinical response in the subject in 8 weeks or less, 6 weeks or less, 30 days or less, 22 days or less, or 8 days or less of starting once a day administration of the suppository to the subject.

The rectal suppository may provide a reduction in Simple Clinical Colitis Activity Index (SCCAI) score of 2 or more, 3 or more, or 4 or more, in the subject in 8 weeks or less, 6 weeks or less, 30 days or less, 22 days or less, 15 days or less, or 8 days or less, of starting once a day administration of the suppository to the subject.

The rectal suppository may provide remission in the subject in 8 weeks or less, 6 weeks or less, 30 days or less, 15 days or less, 8 days or less, of starting once a day administration of the suppository to the subject. Providing remission after starting treatment may be defined as a reduction in Simple Clinical Colitis Activity Index (SCCAI) score in the subject from a score greater than 2 to a score equal to or less than 2, with a reduction in the score of greater than or equal to 3.

The rectal suppository may provide a reduction in Mayo Endoscopic Score (Mayo ES) in the subject of at least 1 point, or at least 2 points in 8 weeks or less, 6 weeks or less, or 30 days or less, of starting once a day administration of the suppository to the subject. For example, the Mayo ES is measured prior to starting once a day treatment and after 8 weeks, 6 weeks, 30 days, or less, of the treatment the Mayo ES is reduced by 1 or 2 points, or more.

The rectal suppository may provide a reduction in ulcerative colitis endoscopic index of severity (UCEIS) score in the subject of at least 1 point, or at least 2 points in 8 weeks or less, 6 weeks or less, or 30 days or less, of starting once a day administration of the suppository to the subject. For example, the ulcerative colitis endoscopic index of severity (UCEIS) score is measured prior to starting once a day treatment and after 8 weeks, 6 weeks, 30 days, or less, of the treatment the ulcerative colitis endoscopic index of severity (UCEIS) score is reduced by 1 point or 2 points or more.

Method of Making Suppository

Described herein is a method of manufacturing a rectal suppository, the method comprising the steps of (a) heating a hard fat to become a liquid hard fat, (b) adding at least one surfactant to the liquid hard fat, (c) adding 6-thioguanine to the liquid hard fat, (d) forming the hard fat into a rectal suppository, wherein step (b) is optionally carried out before step (c) or after step (c).

Examples of the hard fat, surfactant and the 6-thioguanine are described above.

With reference to FIG. 1, at (i) the hard fat is melted to obtain a liquid. The hard fat may be heated to about 40 to 90° C., or about 40 to 80° C., or about 40 to 70° C., about 40 to 65° C., or about 40 to 60° C., or about 20° C. over the melting range of the hard fat, to obtain a liquid hard fat and is optionally stirred or agitated while being heated, for example using overhead stirring.

With reference to FIG. 1, step (ii), comprising adding at least one surfactant to the liquid hard fat, and step (iii) comprising adding 6-thioguanine to the liquid hard fat, may be carried out in either order (for example (ii) before (iii) or (iii) before (ii)) or substantially simultaneously. The heating and/or stirring or agitation may be continued from step (i) during steps (ii) and (iii).

Step (ii), adding at least one surfactant to the liquid hard fat may be carried out prior to (iii) adding 6-thioguanine to the liquid hard fat.

The method may further comprise the step of adding at least one antioxidant to the liquid hard fat. The at least one antioxidant may be added to the liquid hard fat with the surfactant, for example concurrently or consecutively.

The 6-thioguanine may be added to the liquid hard fat in a portion of liquid hard fat, for example, a portion of the liquid hard fat may be removed from the liquid hard fat after the addition of the at least one surfactant and/or at least one antioxidant.

The method may further comprise the step of adding at least one suspending agent to the liquid hard fat. The least one suspending agent may optionally be added to the liquid hard fat prior to the 6-thioguanine. The least one suspending agent may optionally be added to the liquid hard fat prior to, or after the surfactant and optionally prior to or after the antioxidant.

The method may further comprise homogenizing the liquid hard fat after the addition of the 6-thioguanine. The homogenizing may comprise milling and/or high pressure homogenization. For example, wet milling may comprise wet milling the hard fat mixture (comprising the 6-thioguanine and surfactant and optionally the antioxidant and/or suspending agent). Examples of milling include ball milling. Where ball milling is used, the beads may be about 0.1 to 2 mm, or about 1 to 1.5 mm, or about 1.2 to 1.4 mm.

The 6-thioguanine may vary in particle size. Particularly where the 6-thioguanine has a larger particle size (for example D50 about 20 to 100 μm) or a larger particle size distribution, the particle size may be reduced either prior to incorporation into the rectal suppository (for example by dry milling, such as jet milling) or after combining with the liquid hard fat (for example by wet milling).

Milling may be beneficial to homogenize the hard fat and 6-thioguanine (for example to make the distribution of 6-thioguanine throughout the hard fat more consistent) and/or reduce the size of the particles of 6-thioguanine (and/or particles of other components in the suppository), and/or reduce the size distribution of the particles of the 6-thioguanine (and/or particles of other components in the suppository), for example reduce the number of larger particles of 6-thioguanine.

The hard fat may be formed into a rectal suppository by transferring the liquid hard fat into a mold. The hard fat may be cooled to about 31 to 40° C. prior to transferring to the mold, for example about 33 to 35° C. Alternatively, the hard fat may be cooled to about 37 to 40° C. prior to transferring to the mold. The mold may be coated (for example sprayed) with a release aid (for example mineral oil, or another pharmaceutically acceptable release aid) prior to transferring the liquid hard fat into the mold. This may aid with releasing the suppository from the mold once it has cooled/hardened in the mold. Suppositories may be allowed to cool or cooled to about 10 and 25° C. prior to the hardened suppository being released from the mold.

Figure 2:
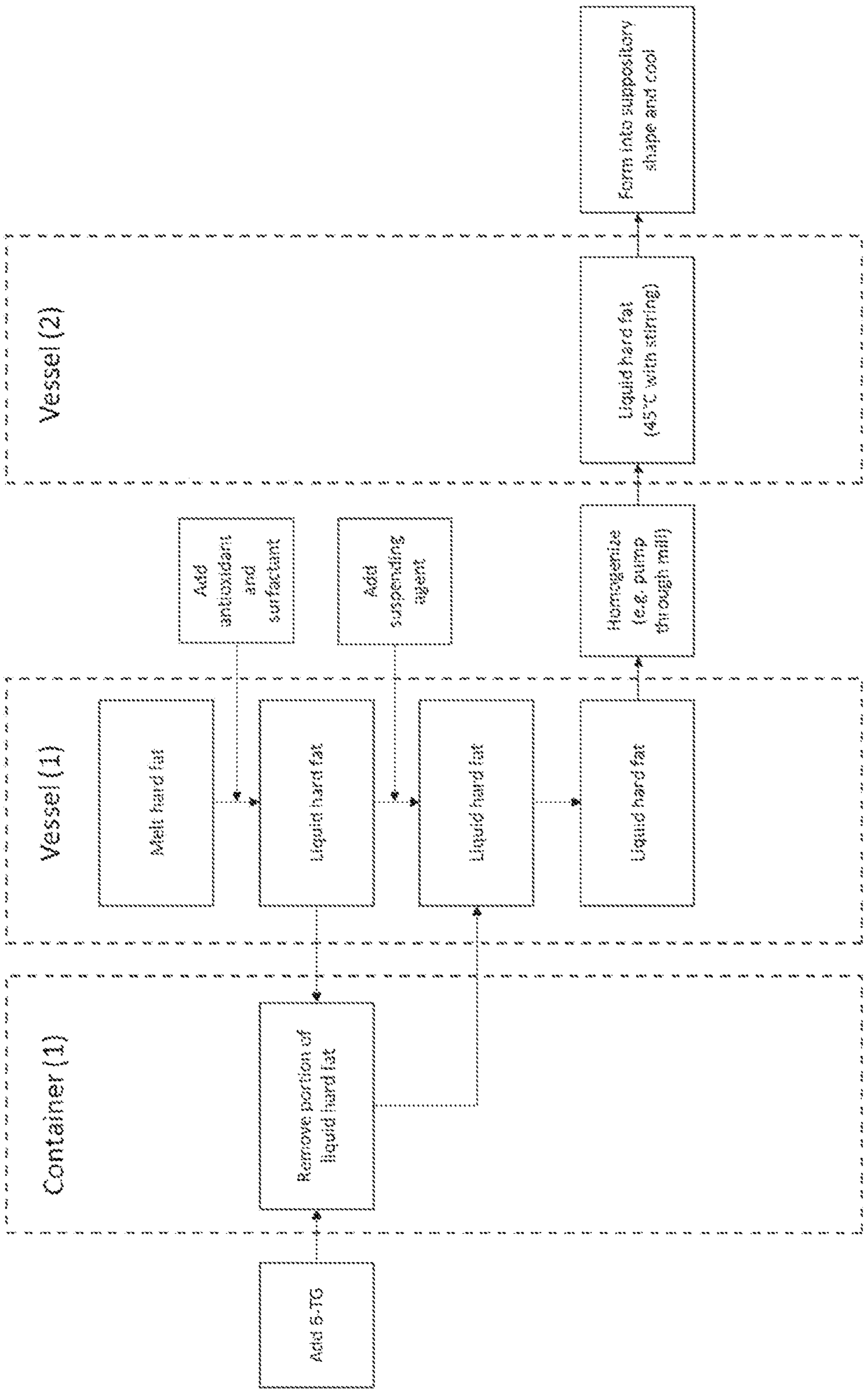
FIG. 2 is a schematic of an example of manufacturing a rectal suppository.

FIG. 2 shows an example of the method of manufacturing a rectal suppository.

After the rectal suppository is manufactured, it may be stored at a temperature below the melting point of the rectal suppository, for example at less than or equal to about 25° C., or less than or equal to about 8° C., or between about 0 and 25° C., or between about 0 and 8° C., or between about 4 and 8° C.

The invention will be illustrated in more detail with reference to the following Examples, but it should be understood that the present invention is not deemed to be limited thereto.

EXAMPLES

Example 1—Comparison of Hard Fats

In vitro dissolution testing may provide an indication of in vivo performance with respect to diffusion and dissolution of the 6-TG from the rectal suppository.

The dissolution of rectal suppositories with various hard fats (and the same level of surfactant) were tested for comparison. The formulations of the rectal suppositories are shown in Table 3. The 6-thioguanine used in Examples 1A, 1B, 2 and 3 was batch B (see Example 4).

TABLE 3

Rectal Suppository Formulations

| | Amount of ingredient - mg/unit (% w/w) Example Number | | | | |
|---|---|---|---|---|---|
| Ingredient | 1A | 1B | 2 | 3 | Comparative 4 |
| 6-Thioguanine | 10.00 (0.50%) | 10.00 (0.50%) | 10.00 (0.50%) | 10.00 (0.50%) | 10.00 (0.50%) |
| Gattefossé Suppocire A | 1980.00 (99.00%) | 1980.00 (98.00%) | — | — | — |
| Gattefossé Suppocire AM | — | — | 1980.00 (99.00%) | — | — |
| Gattefossé Suppocire BM | — | — | — | 1980.00 (99.00%) | — |
| Polysorbate 80 | 10.00 (0.50%) | 30.00 (1.50%) | 10.00 (0.50%) | 10.00 (0.50%) | — |
| Cocoa Butter | | | | | 1990.00 (99.50%) |
| Total | 2000 (100%) | 2000 (100%) | 2000 (100%) | 2000 (100%) | 2000 (100%) |

The dissolutions were measured using the conditions shown in Tables 4 and 5. The dissolution tests were carried out on multiple samples (for example, 3 samples) and the average (mean) dissolution of the samples calculated.

TABLE 4

| Dissolution test conditions | |
|---|---|
| Apparatus: | Baskets (40 mesh), Apparatus 1 |
| Baskets speed: | 100 ± 4 rpm |
| Bath temperature: | 37.0 ± 0.5° C. |
| Volume (mL)/Mass (g) of dissolution medium per vessel: | 900 mL/900 g |
| Sampling time: | 10, 20, 30, 45 and 60 minutes (and 90 minutes*) or as required (*in some instances after 60 minutes, speed was increased to 200 rpm and test run for further 30 minutes, to give a 90 minute (“infinity”) time point). |
| Dissolution Medium: | 0.05M phosphate buffer, pH 6.8: (To prepare 8 L, dissolve about 54.4 g of $KH_2PO_4$ in 7920 mL of purified water. Add 80 mL of 2M sodium hydroxide and mix. Adjust the resulting solution with 2M sodium hydroxide to pH 6.80 ± 0.05.) |
| Sample Volume | 20 mL (withdraw for testing and time points and replace volume with dissolution medium) |

TABLE 5

| UV-Vis Spectrophotometer | |
|---|---|
| Cuvettes: | 10 mm quartz |
| Wavelength of interest for fixed wavelength measurements: | 341 nm (±1 nm), i.e., the wavelength of maximum absorbance |
| UV-Vis source changeover: | 370.0 nm |

Figure 3:
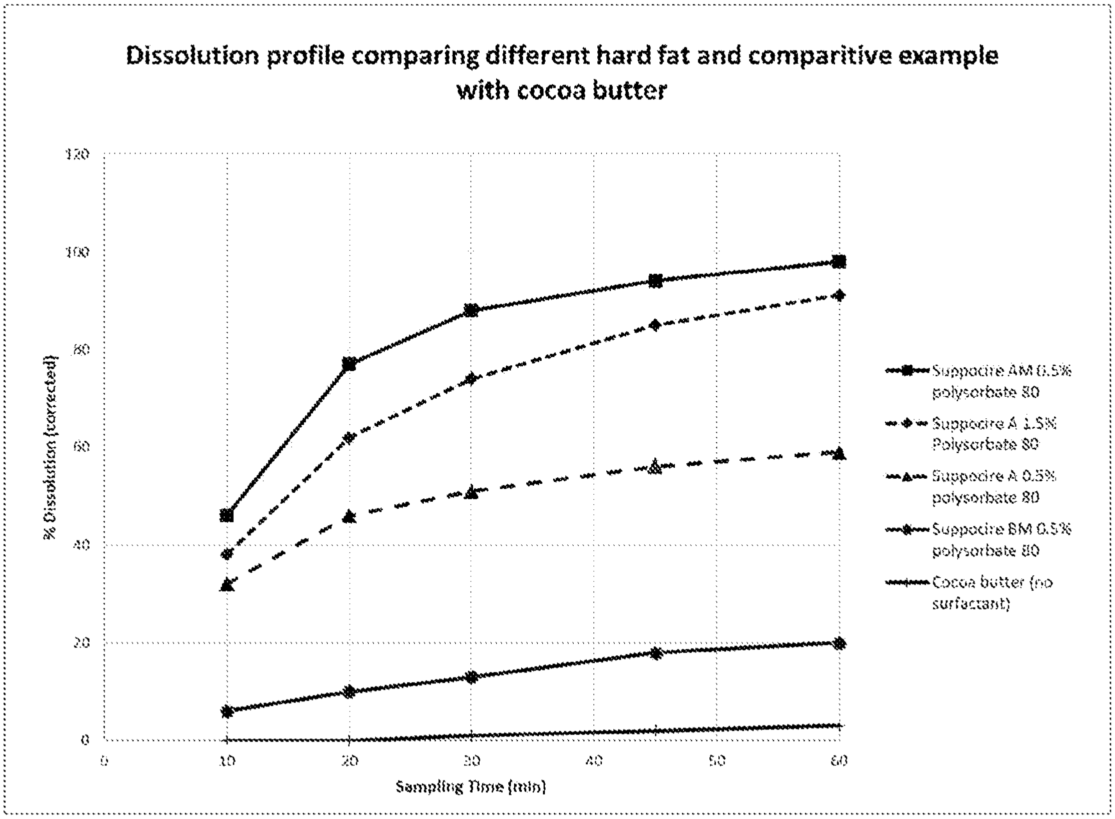
FIG. 3 is a graph showing comparing dissolution of rectal suppository formulations with different hard fats and a comparative example with a suppository made of cocoa butter.

The dissolution results are shown in Table 6 and graphically in FIG. 3.

Suppocire AM with 0.5% surfactant (polysorbate 80) showed the fastest dissolution. Suppocire A with 0.5% surfactant (polysorbate 80) showed slower dissolution, but the dissolution speed was increased so that it was similar to Suppocire AM when an increased amount of surfactant (polysorbate 80) was included (1.5%).

Suppocire BM showed the slowest dissolution under the test conditions. It was noted Suppocire BM has a higher melting range than Suppocire A or AM. The dissolution test was carried out at 37.0 (±0.5° C.), which may have effected the dissolution test result.

For comparison, a suppository made of cocoa butter with no surfactant (but the same level of 6-thiogunaine) showed barely any or very slow dissolution under the test conditions.

TABLE 6

Average % dissolution over time

| Example | Average of % Dissolution (n = 3) Sample Time (mins) | | | | |
|---|---|---|---|---|---|
| | 10 | 20 | 30 | 45 | 60 |
| 1A - Suppocire A | 32 | 46 | 51 | 56 | 59 |
| 1B - Suppocire A (higher surfactant) | 38 | 62 | 74 | 85 | 91 |
| 2 - Suppocire AM | 46 | 77 | 88 | 94 | 98 |
| 3 - Suppocire BM | 6 | 10 | 13 | 18 | 20 |
| 4 - Comparative cocoa butter | 0 | 0 | 1 | 2 | 3 |

Example 2—Comparison of Surfactants

The dissolutions of formulations with different surfactants were tested. The formulations are shown in Table 7. The 6-thioguanine used in Examples 5, 6, 7 and 8 was batch C (see Example 4). The dissolutions tests were performed using the conditions shown in Tables 4 and 5.

TABLE 7

Rectal Suppository formulations

| Ingredient | Amount of ingredient - mg/unit (% w/w) Example number | | | |
|---|---|---|---|---|
| | 5 | 6 | 7 | 8 |
| Thioguanine (API) | 5.39 (0.29%) | 5.39 (0.29%) | 7.18 (0.39%) | 5.18 (0.28%) |
| Suppocire AM | 1816.67 (98.20%) | 1816.67 (98.20%) | 1815.03 (98.11%) | 1816.70 (98.20%) |
| SPAN 80 | 100.00 (1.00%) | — | — | — |
| Brij S20 | — | 18.50 (1.00%) | — | — |
| SPAN 20 | — | — | 18.36 (0.99%) | — |
| Polysorbate 80 | — | — | — | 18.50 (1.00%) |
| Aerosil ™ 200 pharma (silicon dioxide) | 9.25 (0.50%) | 9.25 (0.50%) | 9.24 (0.50%) | 9.25 (0.50%) |
| BHA | 0.19 (0.01%) | 0.19 (0.01%) | 0.18 (0.01%) | 0.19 (0.01%) |
| BHT | — | — | — | 0.19 (0.01%) |
| Total | 1850 (100%) | 1850 (100%) | 1850 (100%) | 1850 (100%) |

Figure 4:
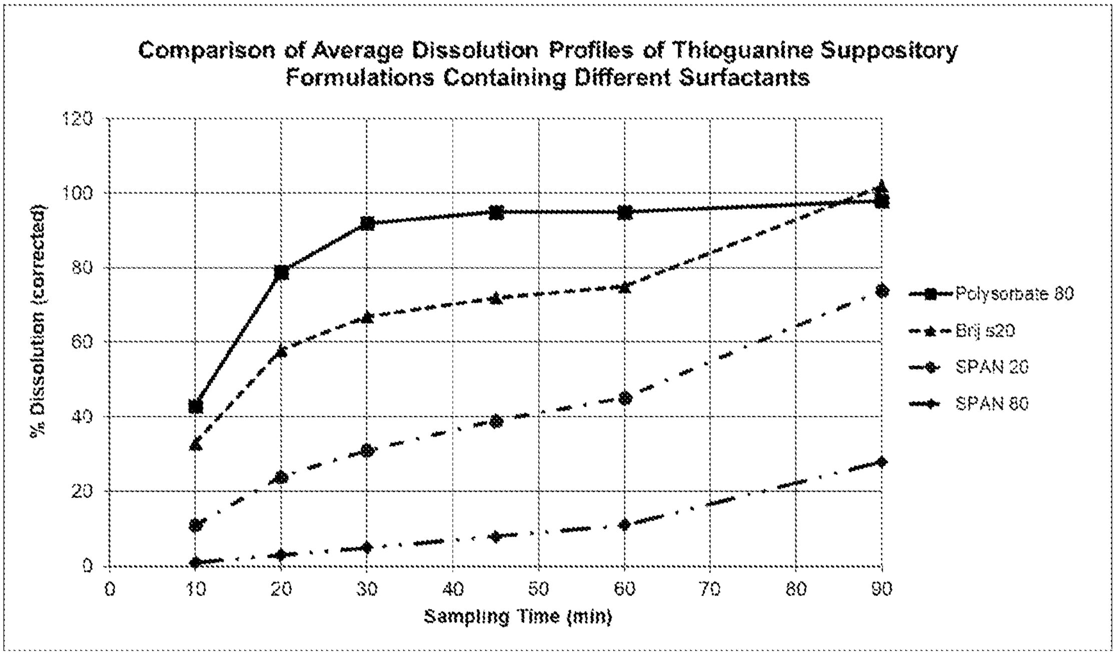
FIG. 4 is a graph comparing dissolution of rectal suppository formulations with different surfactants.

The dissolution results are shown in Table 8 and graphically in FIG. 4.

TABLE 8

| Average of % Dissolution over time | | | | | | |
|---|---|---|---|---|---|---|
| | Average of % Dissolution (n = 3) Sample Time (mins) | | | | | |
| Example | 10 | 20 | 30 | 45 | 60 | 90* |
| 5 - (1% SPAN 80) | 1 | 3 | 5 | 8 | 11 | 28 |
| 6 - (1% Brij S20) | 33 | 58 | 67 | 72 | 75 | 102 |
| 7 - (1% SPAN 20) | 11 | 24 | 31 | 39 | 45 | 74 |
| 8 - (1% polysorbate 80) | 43 | 79 | 92 | 95 | 95 | 98 |

The formulation with 1% SPAN 80 (low HLB of about 4) showed the slowest dissolution. The dissolution was incomplete even at the 90-minute infinity reading. The formulation with 1% SPAN 20 (HLB about 9) showed faster, but still relatively slow and incomplete dissolution.

Polysorbate 80 and Brij S20 both have HLB values of about 15. The formulations with Polysorbate 80 and Brij S20 both showed reasonable dissolution speed. However, the formulation with Polysorbate 80 was the fastest and was complete at around 30 to 45 minutes.

Brij S20 is solid at 37° C. It was believed the Brij S20 melting point may effect its ability to combine with the other ingredients and aid dissolution at 37° C. The 90 minute "infinity" reading of 102% may have indicated some variability (for example, lack of uniformity) in the amount of API in each suppository made with the formulation.

Example 3—Amount of Suspending Agent

It was found, particularly when scaling up, that 6-thioguanine may settle to the bottom of mixing vessels. It was found one way of ameliorating this issue was inclusion of a suspending agent.

Formulations with varying amounts of suspending agent (for example, silicon dioxide) were tested for the uniformity of the dosage of 6-thioguanine. The formulations are shown in Table 9. The 6-thioguanine used in Examples 9-15 was batch A (see Example 4).

TABLE 9

| Rectal Suppository Formulations | | | | | | | |
|---|---|---|---|---|---|---|---|
| | Amount of Ingredient - mg/unit (% w/w) Example Number | | | | | | |
| Ingredient | 9 | 10 | 11 | 12 | 13 | 14 (milled) | 15 (milled) |
| 6-Thioguanine | 5.27 (0.28%) | 5.27 (0.28%) | 5.27 (0.28%) | 5.27 (0.28%) | 5.27 (0.28%) | 5.27 (0.28%) | 5.27 (0.28%) |
| Suppocire AM | 1815.13 (98.12%) | 1812.36 (97.97%) | 1807.73 (97.72%) | 1803.11 (97.47%) | 1798.48 (97.22%) | 1816.98 (98.22%) | 1779.98 (96.22%) |
| Aerosil ™ 200 pharma (silicon dioxide) | 1.85 (0.10%) | 4.63 (0.25%) | 9.25 (0.5%) | 13.88 (0.75%) | 18.50 (1.00%) | — | 18.50 (1.00%) |
| Polysorbate 80 | 27.75 (1.50%) | 27.75 (1.50%) | 27.75 (1.50%) | 27.75 (1.50%) | 27.75 (1.50%) | 27.75 (1.50%) | 27.75 (1.50%) |
| Vitamin E | — | — | — | — | — | — | 18.50 (1.00%) |
| Total | 1850 (100%) | 1850 (100%) | 1850 (100%) | 1850 (100%) | 1850 (100%) | 1850 (100%) | 1850 (100%) |

Figure 5:
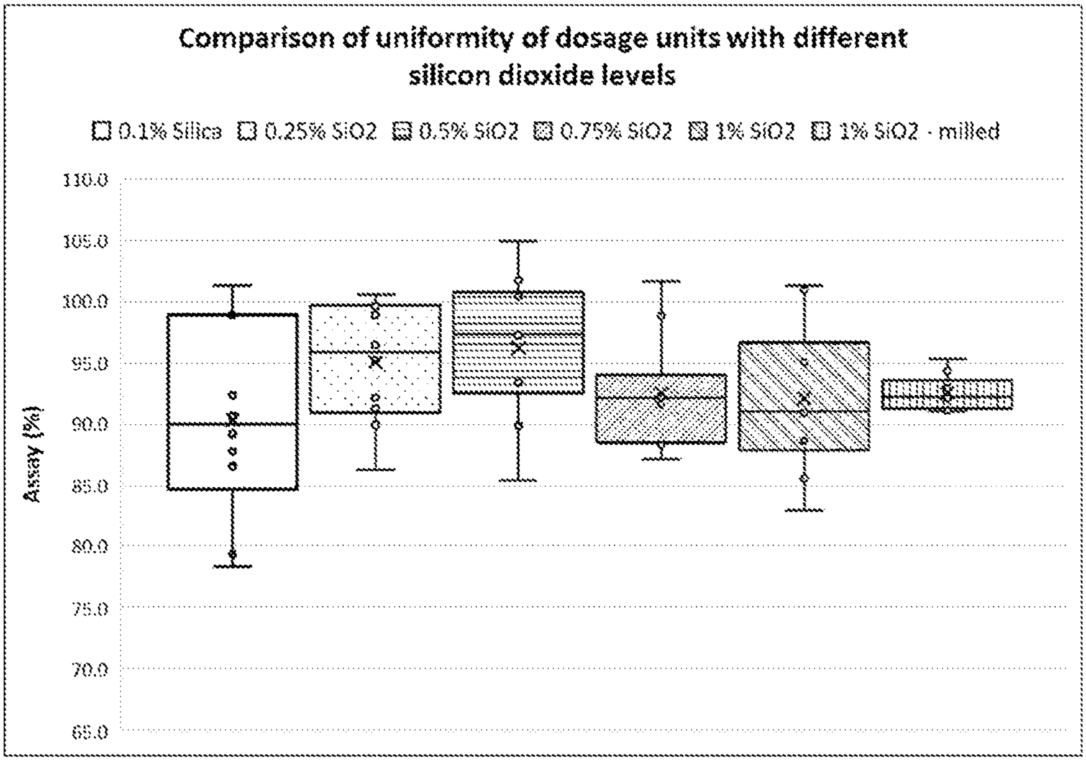
FIG. 5 is a graph comparing uniformity of rectal suppository formulations with different levels of silicon dioxide.

The amount of 6-thioguanine (API) in a batch of ten suppositories of the same formulation were tested by dissolving each suppository in 0.01 M NaOH and purified water and testing the solution using Ultra-High-Performance Liquid Chromatography (UHPLC) compared to reference solutions of 6-thioguanine. The amount of 6-thioguanine in each suppository (mg/unit and % of Label claim (LC), the label claim being 5 mg in this Example), the average and the standard deviation across the batches are shown in Table 10A and B, and graphically in FIG. 5.

Examples 14 and 15 were 9 kg formulation batch which were both one pass milled. As can be seen from the mg/unit, % LC and standard deviation, there was difficulty with Example 14 (without a suspending agent) distributing the 6-thioguanine throughout the formulation and filling/forming consistently into the units (suppositories). Examples 9-13 were 100 g batches which were not milled. Example 9 (containing 0.10% silicon dioxide) improved the standard deviation to 8.7. Higher levels of silicon dioxide further improved the standard deviation. The variability in the amount of API within the unmilled batches of suppositories with 0.25-1% silicon dioxide is similar. The formulation with the lowest standard deviation (1.6) was Example 15 that included 1% silicon dioxide and was milled (homogenised).

The inclusion of a suspending agent and/or milling and/or homogenizing of the formulation provided a way of reducing the variability in the amount of 6-thioguanine across a batch of suppositories of the same formulation. Low variability in a batch of suppositories is desirable for consistent dosing of patients.

TABLE 10A

Comparing uniformity of dosage units (suppositories) with varying levels of $SiO_2$ - weight and water corrected using average suppository mass (ASM) of 1850 mg/suppository

| | Example Number Unmilled | | | | | |
|---|---|---|---|---|---|---|
| | 9 | | 10 | | 11 | |
| Unit no. | Assay (mg/unit) | Assay (% LC) | Assay (mg/unit) | Assay (% LC) | Assay (mg/unit) | Assay (% LC) |
| 1 | 4.33 | 86.5 | 4.95 | 98.9 | 4.88 | 97.5 |
| 2 | 5.07 | 101.3 | 4.61 | 92.1 | 5.02 | 100.4 |
| 3 | 4.53 | 90.6 | 4.31 | 86.2 | 4.49 | 89.9 |
| 4 | 4.94 | 98.9 | 4.56 | 91.3 | 4.27 | 85.4 |
| 5 | 4.62 | 92.3 | 4.50 | 89.9 | 4.86 | 97.2 |
| 6 | 3.97 | 79.3 | 5.01 | 100.1 | 4.69 | 93.9 |
| 7 | 3.92 | 78.3 | 4.76 | 95.2 | 4.67 | 93.4 |
| 8 | 4.95 | 98.9 | 4.98 | 99.6 | 4.88 | 97.7 |
| 9 | 4.39 | 87.8 | 5.03 | 100.6 | 5.09 | 101.7 |
| 10 | 4.46 | 89.2 | 4.82 | 96.5 | 5.25 | 105.0 |
| Mean | 4.52 | 90.3 | 4.75 | 95.0 | 4.81 | 96.2 |
| SD | 8.7 | | 5.2 | | 6.0 | |

TABLE 10B

Comparing uniformity of dosage units (suppositories) with varying levels of $SiO_2$ - weight and water corrected using average suppository mass (ASM) of 1850 mg/suppository

| | Example Number | | | | | | | |
|---|---|---|---|---|---|---|---|---|
| | Unmilled | | | | Milled | | | |
| | 12 | | 13 | | 14 | | 15 | |
| Unit no. | Assay (mg/unit) | Assay (% LC) | Assay (mg/unit) | Assay (% LC) | Assay (mg/unit) | Assay (% LC) | Assay (mg/unit) | Assay (% LC) |
| 1 | 4.62 | 92.4 | 4.75 | 95.0 | 0.39 | 7.8 | 4.57 | 91.3 |
| 2 | 4.36 | 87.2 | 4.56 | 91.2 | 0.60 | 11.9 | 4.61 | 92.1 |
| 3 | 4.60 | 92.1 | 4.45 | 88.9 | 0.82 | 16.4 | 4.62 | 92.3 |
| 4 | 4.58 | 91.6 | 5.06 | 101.3 | 0.81 | 16.1 | 4.57 | 91.5 |
| 5 | 4.62 | 92.3 | 5.05 | 100.9 | 0.93 | 18.5 | 4.56 | 91.1 |
| 6 | 4.94 | 98.9 | 4.43 | 88.7 | 0.79 | 15.7 | 4.66 | 93.2 |
| 7 | 4.61 | 92.2 | 4.15 | 82.9 | 0.54 | 10.8 | 4.72 | 94.4 |
| 8 | 4.42 | 88.3 | 4.54 | 90.9 | 0.78 | 15.6 | 4.77 | 95.3 |
| 9 | 5.08 | 101.6 | 4.76 | 95.2 | 0.63 | 12.7 | 4.65 | 92.9 |
| 10 | 4.42 | 88.5 | 4.28 | 85.6 | 0.59 | 11.8 | 4.55 | 91.0 |
| Mean | 4.63 | 92.5 | 4.60 | 92.1 | 0.69 | 13.0 | 4.63 | 92.5 |
| SD | 4.9 | | 6.6 | | 23.7 | | 1.6 | |

Example 4-6-TG Particle Size

The particles size distribution of the API alone and in the rectal suppository formulations was measured using a Malvern Mastersizer 3000 (Hydro SM). The samples were dispersed in n-heptane containing 0.1% span 80 pre-saturated with 6-thioguanine (to reduce any dissolution of the 6-thioguanine particles in the samples).

The particle size distribution results are shown in Table 11 and the histograms are shown in FIGS. 6A, B, C, D, E, F1 and F2.

The histograms show Volume Density (%) on the y-axis, ranging from 0 to 8 (with markers at 0, 2, 4, 6 and 8) and Size Classes (μm) on the x-axis ranging from 0.01 to 10,000.0 (with markers at 0.01, 0.1, 1.0, 10.0, 100.0, 1,000.0 and 10,000.0).

TABLE 11

Particle size distribution (PSD)

| Sample | Description | D10 (μm) | D50 (μm) | D90 (μm) |
|---|---|---|---|---|
| A | 6-Thioguanine batch A (not in formulation) | 5.4 | 66.8 | 261.0 |
| B | 6-Thioguanine batch B (not in formulation) | 5.3 | 69.1 | 267.0 |
| C | 6-Thioguanine batch C (not in formulation) | 2.9 | 9.0 | 151.0 |
| D | Placebo Formulation (including $SiO_2$ without 6-thioguanine) | 14.5 | 36.5 | 76.0 |
| E (Example 15) | 5 mg Suppository formulation (milled - including $SiO_2$ and 6-thioguanine batch A) | 3.6 | 21.8 | 58.2 |
| F1 | 20 mg unmilled 6-thioguanine suppository formulation (including $SiO_2$, BHA and 6-thioguanine batch C) | 7.5 | 47.4 | 113.0 |
| F2 | 20 mg milled 6-thioguanine suppository formulation (including $SiO_2$, BHA and 6-thioguanine batch C) | 3.8 | 22.1 | 65.3 |

Samples A, B and C were three different batches of 6-thioguanine (not in a suppository formulation). The particle size distribution (PSD) of Sample A and B are similar, but Sample C has a significantly different PSD. The histograms show a minor and major peak for each of Samples A, B and C. In Sample C the major peak appears to be the minor peak in Sample A and B. The PSD of the API may therefore vary.

Sample D was a placebo formulation (including silicon dioxide) without 6-thioguanine (not milled). The particles measured were the silicon dioxide. The D50 is about 36.5 and appears to be positioned between the minor and major peaks of the 6-thioguanine samples. A placebo batch of without silicon dioxide or 6-thioguanine gave no histogram (i.e., no particles were detected).

Sample E was a 5 mg suppository formulation (Example 15, including silicon dioxide and 6-thioguanine batch A) which was milled during manufacture. As both silicon dioxide and 6-thioguanine batch A were present, the expected peaks would correspond to Sample A and D, however the formulation was milled during manufacture. Comparing the histograms, D10, D50 and D90 of Samples A, D and E showed that the particle size of both the silicon dioxide and/or the 6-thioguanine appears to have been reduced by milling.

Sample F1 and F2 were a 20 mg 6-thioguanine suppository formulation (including silicon dioxide, BHA and 6-thioguanine batch C), prior to and after milling. Comparing the histograms, D10, D50 and D90 of Samples C, D and F1, the peaks for silicon dioxide (Sample D) and 6-thioguanaine (Sample C) were seen in the histogram for F1, with the peak corresponding to silicon dioxide (Sample D) appearing to be predominant. Comparing F1 to F2 the D50 and D90 have reduced. However, the particle size reduction may have been due to reduction in the size of the silicon dioxide, rather than the 6-thioguanaine, which already had a lower particle size prior to milling.

Example 5—Amount of Polysorbate 80

The dissolutions of formulations with different levels of polysorbate 80 were tested. The formulations are shown in Table 12. The 6-thioguanine used in Examples 16-22 was batch C (see Example 4).

The dissolutions tests were performed using the using the conditions shown in Tables 4 and 5.

TABLE 12

Rectal Suppository Formulations

| Ingredient | Amount of ingredient - mg/unit (% w/w) Example number 16 | 17 | 18 | 8 | 19 | 20 | 21 | 22 |
|---|---|---|---|---|---|---|---|---|
| 6-TG | 5.18 (0.28%) | 5.18 (0.28%) | 5.18 (0.28%) | 5.18 (0.28%) | 5.18 (0.28%) | 5.18 (0.28%) | 5.18 (0.28%) | 5.18 (0.28%) |
| Suppocire AM | 1835.20 (99.20%) | 1830.76 (98.96%) | 1825.95 (98.70%) | 1816.70 (98.20%) | 1807.45 (97.40%) | 1798.20 (97.20%) | 1788.95 (96.70%) | 1779.70 (96.20%) |
| Aerosil ™ 200 pharma (silicon dioxide) | 9.25 (0.50%) | 9.25 (0.50%) | 9.25 (0.50%) | 9.25 (0.50%) | 9.25 (0.50%) | 9.25 (0.50%) | 9.25 (0.50%) | 9.25 (0.50%) |
| Polysorbate 80 | 0 | 4.63 (0.25%) | 9.25 (0.50%) | 18.50 (1.00%) | 27.75 (1.50%) | 37.00 (2.00%) | 46.25 (2.50%) | 55.50 (3.00%) |
| BHT | 0.19 (0.01%) | 0 | 0.19 (0.01%) | 0.19 (0.01%) | 0.19 (0.01%) | 0.19 (0.01%) | 0.19 (0.01%) | 0.19 (0.01%) |
| BHA | 0.19 (0.01%) | 0.19 (0.01%) | 0.19 (0.01%) | 0.19 (0.01%) | 0.19 (0.01%) | 0.19 (0.01%) | 0.19 (0.01%) | 0.19 (0.01%) |
| Total | 1850 (100%) | 1850 (100%) | 1850 (100%) | 1850 (100%) | 1850 (100%) | 1850 (100%) | 1850 (100%) | 1850 (100%) |

Figure 7:
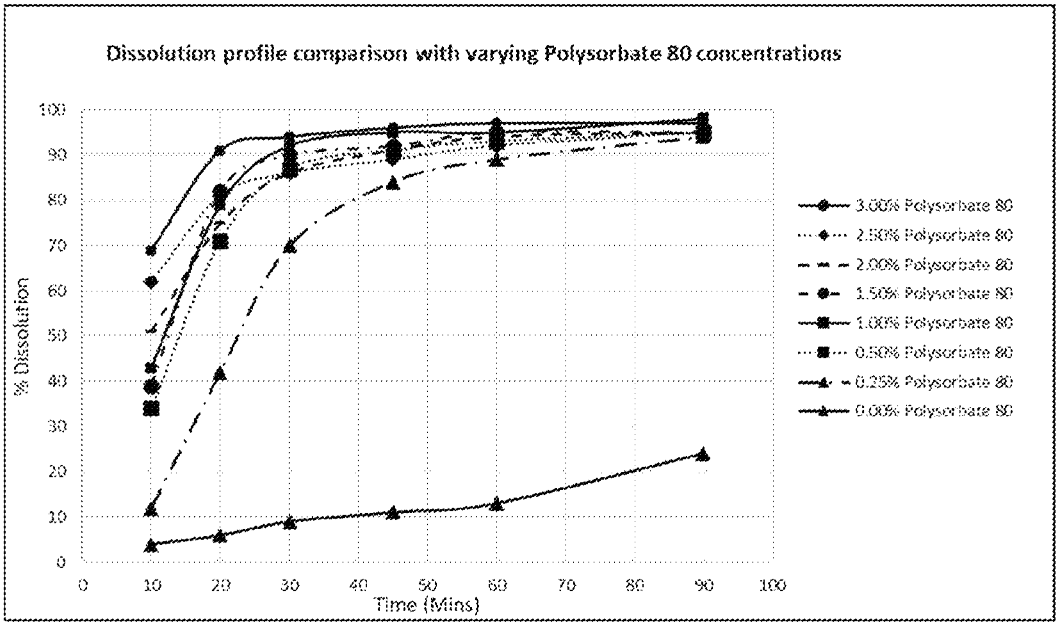
FIG. 7 is a graph comparing dissolution of rectal suppository formulations with different levels of polysorbate 80.

The dissolution results are shown in Table 12 and graphically in FIG. 7.

TABLE 12

Average % dissolution

| Example number | Average of % Dissolution (n = 3) Sample Time (mins) 10 | 20 | 30 | 45 | 60 | 90* |
|---|---|---|---|---|---|---|
| 16 | 4 | 6 | 9 | 11 | 13 | 24 |
| 17 | 12 | 42 | 70 | 84 | 89 | 94 |
| 18 | 34 | 71 | 87 | 91 | 93 | 95 |
| 8 | 43 | 79 | 92 | 95 | 95 | 98 |
| 19 | 39 | 82 | 90 | 92 | 95 | 95 |
| 20 | 51 | 75 | 86 | 91 | 94 | 95 |
| 21 | 62 | 81 | 86 | 89 | 92 | 95 |
| 22 | 69 | 91 | 94 | 96 | 97 | 97 |

The formulation with 0% polysorbate 80 showed only 13% dissolution at 60 minutes.

An improvement in the rate and/or completion of dissolution at 60 minutes was seen when increasing amounts of polysorbate 80 were used, for example, 0.25% polysorbate 80 was slower than 0.5% polysorbate 80 and 1% polysorbate 80 was faster than both 025% and 0.5% polysorbate. However, there was only a small difference seen after 30 minutes between formulations with 1%, 1.5%, 2%, 2.5% and 3% polysorbate 80, with the main difference being initial speed of dissolution (for example, the first 10 minutes).

Example 6—Formulations and Manufacturing Method

Further examples of rectal suppository formulations are shown in Table 13, providing 5 mg, 10 mg and 20 mg of 6-thioguanine per suppository.

TABLE 13

Rectal Suppository Formulations

| Ingredient | Function | Amount of ingredient - mg/unit (% w/w) Example number Example 23 | Example 24 | Example 25 |
|---|---|---|---|---|
| 6-Thioguanine* | API | 5 (0.27%) | 10 (0.54%) | 20 (1.08%) |
| Suppocire AM | Suppository Base (hard fat) | 1817.07 (98.22%) | 1812.07 (97.95%) | 1802.07 (97.41%) |
| Aerosil ™ 200 pharma (silicon dioxide) | Suspending agent | 9.25 (0.50%) | 9.25 (0.50%) | 9.25 (0.50%) |
| Polysorbate 80 | Surfactant | 18.50 (1.00%) | 18.50 (1.00%) | 18.50 (1.00%) |
| BHA | Antioxidant | 0.19 (0.01%) | 0.19 (0.01%) | 0.19 (0.01%) |
| Total | | 1850 (100%) | 1850 (100%) | 1850 (100%) |

*Amount of 6-thioguanine may be adjusted for potency against the USP reference standard.

The following method (for example) may be used for a 20 kg batch size:

1. Dispense the hard fat into the vessel (1), (preferably under yellow light).
2. Heat the fat in vessel (1) to approx. 57° C. with slow stirring, until the mixture is clear and homogenous.
3. Dispense the BHA into vessel (1).
4. Maintain the temperature of the mixture in vessel (1) at 57° C. with slow stirring, until BHA is dissolved.
5. Dispense the Polysorbate 80 into vessel (1).
6. Maintain temperature with slow stirring, until the mixture is homogenous.
7. Dispense approximately 1 kg of mixture from vessel (1) into container (1) and 1 kg into container (2).
8. Dispense 6-thioguanine (hemihydrate) into the container (1) and mix.
9. Dispense the silicon dioxide into vessel (1).
10. Maintain temperature with slow stirring, until the mixture is homogenous.
11. Dispense the contents of container (1) into vessel (1) while mixing. Use the contents of container (2) to rinse container (1) into vessel (1).
12. Lower the temperature to approx. 45° C. while maintaining stirring.
13. Pump the vessel (1) contents through bead mill into vessel (2) (preferably vessel (2) is set to approximately 45° C.) (preferably use heating bands on pump hoses).
14. Maintain mixture at approximately 45° C. while stirring with an overhead stirrer.
15. Pour mixture into hopper of suppository fill machine with agitator switched on and empty suppository shells are mounted on feeder reel (for example Bonapace BP-10 Suppository Filling Machine, set to shell capacity 2.25 cc, fill mass aim 1.85 g, hopper temp 38-40° C.).
16. Run filled suppository shells through Suppository Sealing Machine (for example Bonapace BP-11 Suppository Sealing Machine)

The melting range of the suppositories were measured using a Mettler Toledo automatic tester at 1 atmosphere of pressure. Melting started about 33-34° C. Melting endpoint was somewhat obscured due to the opacity of the suppository but visually appears to be complete by 36° C.

Example 7—Formulations and Manufacturing Method

Further examples of rectal suppository formulations are shown in Table 14, providing 5 mg and 20 mg of 6-thioguanine per suppository at a lower total weight per suppository.

Batch C of 6-thioguanine was used (see Example 4) with particle size distribution D10: 2.9 μm, D50: 9.0 μm, D90: 151.0 μm. The manufacturing method did not include a milling step.

TABLE 14

Rectal Suppository Formulations

| Ingredient | Function | Amount of ingredient - mg/unit (% w/w) Example number<br>Example 26 | <br>Example 27 |
|---|---|---|---|
| 6-Thioguanine* (Batch C) | API | 5.0 (0.5%) | 20 (2.0%) |
| Suppocire AM | Suppository Base (hard fat) | 980.0 (98.0%) | 965.0 (96.5%) |
| Aerosil ™ 200 pharma (silicon dioxide) | Suspending agent | 5.0 (0.50%) | 5.0 (0.50%) |
| Polysorbate 80 | Surfactant | 10.0 (1.0%) | 10.0 (1.0%) |
| Total | | 1000 (100%) | 1000 (100%) |

*Amount of 6-thioguanine may be adjusted for potency against the USP reference standard.

The following method was used to make the rectal suppositories:

1. Hard fat (Suppocire AM) was weighted into a vessel and heated to about 57° C.
2. While maintaining the temperature at about 57° C., surfactant (polysorbate 80) was added to the liquid/molten hard fat and stirred using a stirrer or homogeniser at a low speed. For example, mixing may be using a homogeniser, or mixing may be mechanical stirring. An example of low speed is about 50 to 200 rpm mechanical mixing or about 1000 rpm for homogenising, but may vary depending on the apparatus used.
3. The surfactant (polysorbate 80) and liquid/molten hard fat were mixed together for about 5 minutes.
4. The temperature was maintained and suspending agent (Aerosil 200 pharma) was added with stirring/homogenising at a low speed.
5. Stirring/homogenising was continued and the temperature of the liquid/molten mixture was reduced to about 45° C.
6. With the liquid/molten mixture stirring/homogenising at 45° C., the 6-thioguanine was added and allowed to disperse.
7. Once the 6-thioguanine is dispersed (for example, no visible agglomerates), the stirring/homogenising speed was raised to a high speed to break unseen agglomerates without substantially introducing air/bubbles to the mixture. The stirring/homogenising was continued in this fashion for about 10 to 15 minutes. For example, where mixing is homogenising a high speed may be 4000 rpm+, or mechanical stirring may be about 1000-2000 rpm. The speeds may vary depending on the apparatus used.
8. Molds were prepared for filling and then set aside. Molds may be sprayed or coated with a release aid (for example mineral oil) to aid release of suppositories.
9. The stirring rate was reduced to low and the temperature reduced to 35° C.
10. The molds were filled with the liquid/molten mixture. The filling temperature for the liquid/molten mixture was about 33° C. Note: If mixture dropped below 30° C. during filling, it must not be reheated and should be discarded.
11. Suppositories were allowed to cool to about 10 and 25° C. The hardened suppositories were then released from the molds.

Example 8—Study Protocol

1. Objectives and Outcomes

The main objective of the study is to assess tolerability, pharmacokinetics, and pharmacodynamics of the 6-thioguanine rectal suppositories in patients with ulcerative proctitis that is refractory to other treatments.

Outcomes to be assessed are set out in Table 15.

TABLE 15

| Outcomes | |
|---|---|
| Primary Outcome 1 | Improvement in inflammatory bowel disease symptoms |
| Assessment method 1 | Simple Clinical Colitis Activity Index (SCCAI) questionnaire |
| Timepoint 1 | SCCAI at days 1, 8, 15, 22, and 29 post-commencement of thioguanine suppositories. |
| Primary outcome 2 | Improvement in colitis activity determined by endoscopic appearance |
| Assessment method 2 | Flexible sigmoidoscopy |
| Timepoint 2 | Day 29 |
| Secondary outcome 1 | Pharmacokinetics including AUC, $C_{max}$, $T_{max}$, Clearance and half-life |
| Assessment method 1 | Blood and rectal tissue samples |
| Timepoint 1 | Blood samples drawn at 30 min, 1, 2, 4, and 6 hours post thioguanine suppository administration days 1 and 29.<br>Flexible sigmoidoscopy for disease activity by Mayo and UCEIS (ulcerative colitis endoscopic index of severity) scores at baseline and on day 29. |

2. Study Design—Patients Administered Thioguanine Rectal Suppositories 2.1. Patient Inclusion, Exclusion and Consent This part of the study will include seven patients in Canterbury and Auckland with refractory ulcerative proctitis. Written informed consent will be obtained from the patients to have thioguanine 20 mg (5 patients) or 5 mg (2 patients) suppository treatment daily for 28 days. Following the first suppository administration, blood samples will be taken for thioguanine pharmacokinetics. At 29 days, blood samples will be taken and flexible sigmoidoscopy performed to take rectal biopsies and further blood samples. Inclusion criteria will include having active ulcerative proctitis on colonoscopy or flexible sigmoidoscopy within 2 months prior to study entry. The patients will have time to consider their decision and someone to talk to with questions. A baseline flexible sigmoidoscopy will be offered to participants who have not had a colonoscopy or flexible sigmoidoscopy within 2 months.

Patients will be excluded during the trial if they experience adverse events that are thought to be related to the thioguanine suppository treatment. Patients will be advised to contact their local principal investigator by phone if they are experiencing an adverse event. Possible adverse events include leukopenia, alopecia, nausea/vomiting.

Patients will not be on a thiopurine drug (azathioprine, 6-mercaptopurine, oral thioguanine) during the study and for at least 4 weeks before the study. They can continue on other IBD treatments (5-ASAs, prednisone, biologic drugs) during the study.

2.2. Thioguanine Rectal Suppository Administration

The study subjects will be provided with 28×20 mg or 5 mg suppositories of 6-thioguanine (made according to Example 7). The first two patients will have either the 5 or 20 mg dose, chosen by computer randomisation. One of the following 5 patients will receive the 5 mg dose, chosen by randomisation, with the rest receiving 20 mg. The subjects will be instructed to insert the suppositories rectally each evening for 28 days.

2.3. Days of Sample Collection

Day 1—Patients will attend Southern Endoscopy Centre (Christchurch, NZ) or Shore Surgery (Auckland, NZ). An intravenous catheter will be placed in the arm or back of the hand. Prior to the first suppository administration a blood sample will be taken as a baseline time 0 pharmacokinetic sample. Following administration of the first suppository, blood samples will be collected at 30 min, 1, 2, 4 and 6 hours post suppository dose to analyse plasma TG and red blood cell (RBC) 6TGN.

At day 28, 24 hours prior to the day 29 flexible sigmoidoscopy, patients will administer a thioguanine suppository. On the morning of day 29, subjects will present to the Southern Endoscopy Centre (SEC) (Christchurch, NZ), or Shakespeare Gastroenterology (SG), Shore Surgery, (Auckland, NZ). On arrival at SEC or SG, patients will be given a Fleet enema (laxative enema) to clear the rectum before endoscopy. An intravenous catheter will be placed in the arm or back of the hand and a baseline blood test will be collected to analyse the concentration of TG in the blood and 6TGN in red blood cells (RBC). Patients will then transfer to the endoscopy room.

At flexible sigmoidoscopy the rectum will be washed thoroughly with saline through the endoscope and suctioned to remove any residual faecal material and any residual Fleet enema liquid. Once the rectum has been thoroughly lavaged and suctioned, 12 small biopsies will be taken throughout the rectum and placed in a polypropylene container containing saline and DTT as below in assay methodology. The polypropylene container will then be immediately placed in liquid nitrogen to snap freeze and transported to a −80° C. freezer for later analysis.

After flexible sigmoidoscopy has been completed, a 20 mg or 5 mg thioguanine suppository will be administered rectally. Blood samples will be collected at 30 min, 1, 2, 4 and 6 hours post suppository dose to analyse plasma TG and red blood cell (RBC) 6TGN.

2.4. Efficacy and Safety Signals, and Compliance

To determine any preliminary efficacy signal, the SCCAI (simple clinical colitis activity index) for each patient will be assessed at day 1 baseline, 8, 15 and 29 days. Day 8 and 15 visits will be in-person or via telehealth appointment with the investigator or study nurse, including SCCAI score and safety check. Faecal calprotectin levels will be requested at day 1 and day 28 as a secondary biomarker of inflammation. The endoscopic subscore of the Mayo score and UCEIS score will be used to grade severity of proctitis at endoscopy at baseline and at day 29. Any treatment emergent adverse events will be recorded at the times of SCCAI recording or at any other times between days 0 and 29. In particular, patients will be asked if they have experienced any new gastrointestinal symptoms including increased rectal discomfort, or any other new symptoms.

When given orally in similar doses to those used in this study, possible side effects from 6-thioguanine include abnormal liver function tests, low blood counts, nausea and/or vomiting, skin rash and infections. Monitoring for these adverse effects is by questionnaire at weekly review and by weekly blood testing.

Patients will be asked to keep a diary of study drug administration and return any unused study drug on day 29.

2.5. Blood Sampling

On day 1 and on the day of the flexible sigmoidoscopy (day 29), an IV cannula will be inserted on arrival at SEC or SG and 5 ml blood in EDTA tube will be collected prior to suppository administration. Further 5 ml blood samples will be collected after suppository administration at 30 minutes, 1, 2, 4 and 6 hours. Plasma and RBCs will be separated by centrifuge and stored at −80° C. for later assay for thioguanine and for 6-thioguanine nucleotides.

2.6 Breast Milk Sampling

For relevant patients, breast milk will be collected on the day of the flexible sigmoidoscopy (day 29) from both breasts. The breast milk will be collected just prior to suppository administration and at 2, 6 and 9 hours post-dose. The breast milk will be transported at 4° C. for later assay for thioguanine and for 8-thioguanine nucleotides.

3. Sample Storage

Sample storage will be in a −80° C. freezer.

4. 6-Thioguanine and Metabolites Assays

Refer to the later section on LC-MS/MS methodology.

5. Summary: Visit Schedule for Study Sites:

Summary of visit schedule for study sites is shown in Table 16.

TABLE 16

| visit schedule for study sites | | | | |
|---|---|---|---|---|
| Day | Visit | SCCAI score | Endoscopy | Bloods |
| Pre-study | preliminary check for suitability | | Complete + Mayo + UCEIS score | Routine + calprotectin |
| 1 | Visit 1: consent and enrolment.<br>Self admin 1 × suppository | Complete | | Bloods on arrival, then 30 min, 1, 2, 4, and 6 h post suppository administration |
| 2 | Self admin 1 × suppository | | | |
| 3 | Self admin 1 × suppository | | | |
| 4 | Self admin 1 × suppository | | | |
| 5 | Self admin 1 × suppository | | | |
| 6 | Self admin 1 × suppository | | | |
| 7 | Self admin 1 × suppository | | | |
| 8 | Self admin 1 × suppository<br>Visit 2: safety check investigator or study nurse | Complete | | |
| 9 | Self admin 1 × suppository | | | |
| 10 | Self admin 1 × suppository | | | |
| 11 | Self admin 1 × suppository | | | |
| 12 | Self admin 1 × suppository | | | |
| 13 | Self admin 1 × suppository | | | |
| 14 | Self admin 1 × suppository | | | |
| 15 | Visit 3: Safety check investigator or study nurse | Complete | | |
| 16 | Self admin 1 × suppository | | | |
| 17 | Self admin 1 × suppository | | | |
| 18 | Self admin 1 × suppository | | | |
| 19 | Self admin 1 × suppository | | | |
| 20 | Self admin 1 × suppository | | | |
| 21 | Self admin 1 × suppository | | | |
| 22 | Self admin 1 × suppository | Complete | | |
| 23 | Self admin 1 × suppository | | | |
| 24 | Self admin 1 × suppository | | | |
| 25 | Self admin 1 × suppository | | | |
| 26 | Self admin 1 × suppository | | | |
| 27 | Self admin 1 × suppository | | | |
| 28 | Self admin 1 × suppository | | | Calprotectin |
| 29 | Visit 4: Last visit + safety check investigator or study nurse<br>Return unused suppositories | Complete | Flexible sigmoidoscopy + samples, Mayo + UCEIS. Suppository inserted after flexible sigmoidoscopy | Bloods on arrival, then post flexible sigmoidoscopy: 30 min, 1, 2, 4, and 6 h post administration of suppository |

6. Control Patients

The concentrations of thiopurines and their metabolites in rectal or colonic tissue is unknown in patients taking oral thiopurine drugs for inflammatory bowel disease and so there is no baseline with which to compare the results found in the preceding study. Therefore, tissue drug and metabolite concentrations are required from a control group of patients.

6.1. Patient Inclusion, Exclusion and Consent

This part of the study will include eight patients in Canterbury and Auckland, New Zealand who are having routine diagnostic colonoscopy. Four patients will have been on oral thioguanine 20 mg daily for at least 4 weeks. Two patients will have been on oral azathioprine for at least 4 weeks. Two patients will have been on no thiopurine treatment for at least 4 weeks. Patients will be aged 18-65 years, male or female.

Written informed consent will be obtained from the patients to have 4 sets of biopsies taken from the rectum and colon in addition to any other biopsies that are required for diagnostic purposes.

At colonoscopy the biopsy sites in the rectum and colon will be washed with saline through the endoscope and suctioned to remove any residual faecal material. A total of 12 small biopsies will be taken and placed in polypropylene containers containing saline and DTT as below in assay methodology. The polypropylene containers will then be immediately placed in liquid nitrogen to snap freeze and transported to a −80° C. freezer for later analysis.

7. LC-MS/MS Methods for Analysis of 6-TG in Plasma, Red Blood Cells (RBC) & Colonic Tissue—(Mei Zhang, Sep. 22, 2021)

The samples of whole blood and colonic biopsy tissue from patients will be sent to the laboratory of Clinical Pharmacology, Department of Medicine, University of Otago—Christchurch (in Toxicology, Canterbury Health Laboratories), New Zealand for the analysis of 6-TG concentrations in plasma, RBC and colonic tissue.

7.1 Sample Collection 7.1.1. Whole Blood in EDTA Tube for Plasma and RBC Samples 1. The method uses 0.2 mL of plasma and 0.2 mL of packed RBC for the determination of 6-TG in plasma and in RBC, respectively. To ensure that repeat analysis can be made if necessary, collect 5.0 mL of whole blood (EDTA tube).
2. Separate plasma and RBC by centrifugation.
3. Transfer plasma to a new polypropylene tube and store plasma samples at −80° C. until transportation to laboratory for the analysis of 6-TG concentrations.

4. Wash the isolated RBC twice in two volumes of saline and centrifuge at 1,250 g for 5 min.
5. Count the number of washed RBCs.
6. Transfer the washed RBC to a new polypropylene tube and store washed RBC samples at −80° C. until transportation to laboratory for the analysis of 6-TG concentrations.
7. Deliver plasma and RBC samples to Toxicology, Canterbury Health Laboratories (NZ) on dry ice to keep frozen.

7.1.2. Colonic Biopsy Tissue

1. Collect colonic biopsy tissue into a polypropylene tube.
2. Rinse the tissue sample in saline in order to remove the extraneous blood and liquid.
3. Store tissue samples at −80° C. until transportation to laboratory for the analysis of 6-TG concentrations.
4. Deliver samples to Toxicology, Canterbury Health Laboratories (NZ) on dry ice to keep frozen.

7.2 API 4000 LC-MS/MS System and Analytical Conditions

Shimadzu LC-20AD HPLC system (Shimadzu Corporation, Kyoto, Japan) interfaced with an API 4000™ triple quadrupole mass spectrometer (Applied Biosystems, Foster City, Canada) equipped with a TurboIonSpray® source Optimized precursor-to-product ion transitions, declustering potential (DP), collision energy (CE) and collision cell exit potential (CXP) of 6-TG and its isotopically labelled internal standard, 6-TG-$^{13}$C2, $^{15}$N.

TABLE 17

| Compound | Precursor Ion (m/z) | Product Ion (m/z) | DP (volts) | CE (volts) | CXP (volts) |
|---|---|---|---|---|---|
| 6-TG | 168 | 151 | 86 | 29 | 10 |
| 6-TG-$^{13}$C2, $^{15}$N | 171 | 154 | 56 | 29 | 24 |

The MS is operated in the positive ion mode with curtain gas, Gas 1 and Gas 2 flow rates of 20, 45 and 60 psi, respectively. The ion spray voltage is 5000 V and the source temperature is 500° C.

Analyst software (Applied Biosystems, Foster City, Canada) used to control equipment, coordinate data acquisition, and analyse data.

Analytical column: Phenomenex Luna C18(2) (50×2.0 mm ID; 5 μm) (Phenomenex, Torrance, CA, USA).

Mobile phase: Solvent A (0.05% formic acid) and solvent B (methanol) for a 6 min gradient elution with 0.3 mL/min flow rate to resolve 6-TG and its isotopically labelled internal standard, 6-TG-$^{13}$C2, $^{15}$N on the analytical column. The gradient elution is shown in Table 18.

TABLE 18

Gradient elution table

| Time (min) | Mobile phase A (%) | Mobile phase B (%) |
|---|---|---|
| 0.0 | 100 | 0 |
| 1.0 | 99 | 1 |
| 1.5 | 20 | 80 |
| 3.5 | 20 | 80 |
| 4.0 | 100 | 0 |
| 6.0 | 100 | 0 |

7.2.1 Chromatogram of 6-TG

Figure 8:
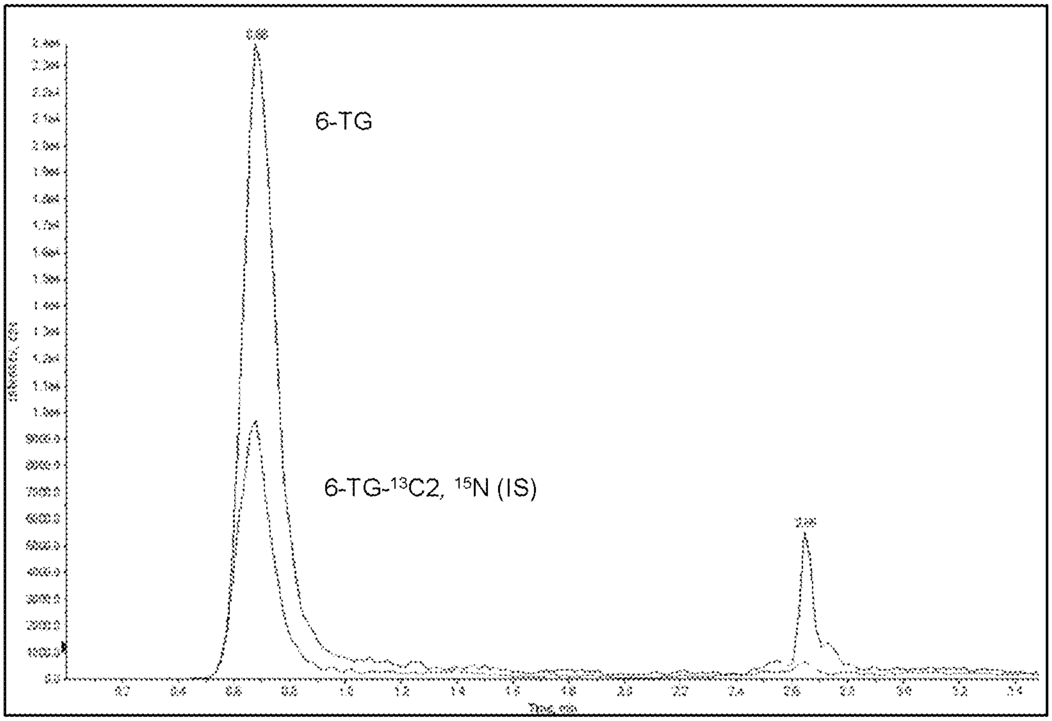
FIG. 8 is a chromatogram of 6-TG.

A chromatogram of 6-TG is shown in FIG. 8.

7.3. Materials

6-TG, dimethylsulfoxide (DMSO), DL-dithiothreitol (DTT), sodium chloride and ammonium bi-carbonate were obtained from Sigma Chemical Company (St. Louis, MO, USA).

Isotope labeled internal standard, 6-thioguanine-$^{13}$C2, $^{15}$N (6-TG-$^{13}$C2, $^{15}$N) was obtained from Toronto Research Chemicals (Toronto, Canada).

70% Perchloric acid, HPLC-grade acetonitrile, methanol and formic acid were purchased from British Drug Houses (Poole, UK).

Phosphate buffered saline pH 7.3 (Dulbecco A) was purchased from Oxoid (Basingstoke, UK).

Distilled, deionised water was produced by a Milli-Q Reagent Water System (Millipore, MA, USA).

The drug-free human plasma and RBCs used as the assay blank and for the preparation of standard curves and quality controls (QCs) were obtained from New Zealand Blood Services (Christchurch, New Zealand).

The drug-free colonic tissue used as the assay blank and for the preparation of standard curve and quality controls (QCs) will be obtained from the Department of Gastroenterolog, Christchurch Hospital (Christchurch, New Zealand).

7.4. Preparation of Solutions 10 mg/0.9 mL DL-dithiothreitol (DTT) in Water—Dissolve 11.1 grams of DTT in 1000 mL of distilled water in a volumetric flask.

Saline (0.9% Sodium chloride in Water)—Dissolve 9.0 grams of sodium chloride in 1000 mL of distilled water in a volumetric flask. Stored at 4° C.

300 mM Ammonium bi-carbonate ($NH_4HCO_3$, ABC) in Water—Dissolve 23.73 g ABC in 1.0 L water. Stored at 4° C.

0.05% Formic acid in Water—Dilute 500 μL of formic acid (BDH, 98/100%) in 1000 mL of distilled water in a volumetric flask.

Washed drug-free red blood cells (RBC):

1. Collect drug-free RBC from New Zealand Blood Services.
2. Wash RBC twice in two volumes of saline and centrifuge at 1,250 g for 5 min.
3. Count washed RBCs and adjust RBC concentration to $8\times10^8$ red cells/0.1 mL RBC solution with saline.
4. Stored blank washed RBC solution at −80° C. until use.

Drug-free colonic tissue homogenate:

1. Collect blank colonic tissue from the Department of Gastroenterology, Christchurch Hospital (NZ). Weigh blank colonic tissue.
2. Add four-fold (w/w) cold PBS to process the homogenization using the Omni Tissue Homogenizer (Omni International, Kennesaw GA, USA).
3. Stored blank colonic tissue homogenate at −80° C. until use.

7.5. Preparation of Standard Solutions

6-TG Stock Solution (0.5 mg/mL)—Dissolve 10 mg of 6-TG in 20 mL of a 1:1 mixture of methanol and dimethylsulfoxide (DMSO) in a volumetric flask. Two sets of 6-TG stock solution will be prepared for standard curve and for quality control (QC) samples respectively. All the stock solutions will be stored at −80° C.

6-TG Intermediate Standard Solution (0.1 mg/mL in water)—Dilute 200 μL of 0.5 mg/mL 6-TG stock solution to 1.0 mL with distilled water. Store at −80° C.

6-TG-$^{13}$C2, $^{15}$N (Internal Standard) Stock Solution (1.0 mg/mL)—Add 1.0 mL of 1:1 mixture of methanol and DMSO into 1.0 mg 6-TG-$^{13}$C2, $^{15}$N vial. Store at −80° C.

Working Internal Standard Solution (1.0 μg/mL in 0.1 M HCl)—Add 50 μL of 1.0 mg/mL 6-TG-$^{13}C2$, $^{15}N$ stock solution to 50 mL of 0.1 M HCl. Store at −80° C.

7.6. Preparation of Standard Curve and QCs for Analysis of Plasma Samples Standard Curve (ST) of 6-TG in Plasma:

1. ST6 (400 ng/0.1 mL): Dilute 200 μL of 6-TG intermediate standard solution (0.1 mg/mL 6-TG in water) to 5.0 mL with drug-free plasma in a volumetric flask. Store at −80° C. in 100 μL aliquots.
2. ST5 (200 ng/0.1 mL): Mix 1.0 mL of ST 6 with 1.0 mL of drug-free plasma. Store at −80° C. in 100 μL aliquots.
3. ST4 (100 ng/0.1 mL): Mix 1.0 mL of ST 5 with 1.0 mL of drug-free plasma. Store at −80° C. in 100 μL aliquots.
4. ST3 (50 ng/0.1 mL): Mix 1.0 mL of ST 4 with 1.0 mL of drug-free plasma. Store at −80° C. in 100 μL aliquots.
5. ST2 (25 ng/0.1 mL): Mix 1.0 mL of ST 3 with 1.0 mL of drug-free plasma. Store at −80° C. in 100 μL aliquots.
6. ST1 (10 ng/0.1 mL): Mix 1.0 mL of ST 2 with 1.25 mL of drug-free plasma. Store at −80° C. in 100 μL aliquots.

QCs of 6-TG in Plasma:

1. QC 3 (400 ng/0.1 mL): Dilute 200 μL of 6-TG intermediate standard solution (0.1 mg/mL 6-TG in water) to 5.0 mL with drug-free plasma in a volumetric flask. Store at −80° C. in 100 μL aliquots.
2. QC 2 (100 ng/0.1 mL): Mix 1.0 mL of QC 3 with 3.0 mL of drug-free plasma. Store at −80° C. in 100 μL aliquots.
3. QC 1 (10 ng/0.1 mL): Mix 0.5 mL of QC 2 with 4.5 mL of drug-free plasma. Store at −80° C. in 100 μL aliquots.

7.7. Preparation of Standard Curve and QCs for Analysis of RBC Samples Standard Curve (ST) of 6-TG in RBC:

1. ST6 (400 ng/8x$10^8$ RBC/0.1 mL): Dilute 200 μL of 6-TG intermediate standard solution (0.1 mg/mL 6-TG in water) to 5.0 mL with washed drug-free RBC solution (8x$10^8$ RBC/0.1 mL RBC solution) in a volumetric flask. Store at −80° C. in 100 μL aliquots.
2. ST5 (200 ng/8x$10^8$ RBC/0.1 mL): Mix 1.0 mL of ST 6 with 1.0 mL of washed drug-free RBC solution. Store at −80° C. in 100 μL aliquots.
3. ST4 (100 ng/8x$10^8$ RBC/0.1 mL): Mix 1.0 mL of ST 5 with 1.0 mL of washed drug-free RBC solution. Store at −80° C. in 100 μL aliquots.
4. ST3 (50 ng/8x$10^8$ RBC/0.1 mL): Mix 1.0 mL of ST 4 with 1.0 mL of washed drug-free RBC solution. Store at −80° C. in 100 μL aliquots.
5. ST2 (25 ng/8x$10^8$ RBC/0.1 mL): Mix 1.0 mL of ST 3 with 1.0 mL of washed drug-free RBC solution. Store at −80° C. in 100 μL aliquots.
6. ST1 (10 ng/8x$10^8$ RBC/0.1 mL): Mix 1.0 mL of ST 2 with 1.25 mL of washed drug-free RBC solution. Store at −80° C. in 100 μL aliquots.

QCs of 6-TG in RBC:

1. QC 3 (400 ng/8x$10^8$ RBC/0.1 mL): Dilute 200 μL of 6-TG intermediate standard solution (0.1 mg/mL 6-TG in water) to 5.0 mL with washed drug-free RBC solution (8x$10^8$ RBC/0.1 mL RBC solution) in a volumetric flask. Store at −80° C. in 100 μL aliquots.
2. QC 2 (100 ng/8x$10^8$ RBC/0.1 mL): Mix 1.0 mL of QC 3 with 3.0 mL of washed drug-free RBC solution. Store at −80° C. in 100 μL aliquots.
3. QC 1 (10 ng/8x$10^8$ RBC/0.1 mL): Mix 0.5 mL of QC 2 with 4.5 mL of washed drug-free RBC solution. Store at −80° C. in 100 μL aliquots.

7.8. Preparation of Standard Curve and QCs for Analysis of Colonic Tissue Samples Standard Curve (ST) of 6-TG in Colonic Tissue 1. ST6 (400 ng/0.1 mL): Dilute 200 μL of 6-TG intermediate standard solution (0.1 mg/mL 6-TG in water) to 5.0 mL with blank colonic tissue homogenate in a volumetric flask. Store at −80° C. in 100 μL aliquots.
2. ST5 (200 ng/0.1 mL): Mix 1.0 mL of ST 6 with 1.0 mL of blank colonic tissue homogenate. Store at −80° C. in 100 μL aliquots.
3. ST4 (100 ng/0.1 mL): Mix 1.0 mL of ST 5 with 1.0 mL of blank colonic tissue homogenate. Store at −80° C. in 100 μL aliquots.
4. ST3 (50 ng/0.1 mL): Mix 1.0 mL of ST 4 with 1.0 mL of blank colonic tissue homogenate. Store at −80° C. in 100 μL aliquots.
5. ST2 (25 ng/0.1 mL): Mix 1.0 mL of ST 3 with 1.0 mL of blank colonic tissue homogenate. Store at −80° C. in 100 μL aliquots.
6. ST1 (10 ng/0.1 mL): Mix 1.0 mL of ST 2 with 1.25 mL of blank colonic tissue homogenate. Store at −80° C. in 100 μL aliquots.

QCs of 6-TG in Colonic Tissue

1. QC 3 (400 ng/0.1 mL): Dilute 200 μL of 6-TG intermediate standard solution (0.1 mg/mL 6-TG in water) to 5.0 mL with blank colonic tissue homogenate in a volumetric flask. Store at −80° C. in 100 μL aliquots.
2. QC 2 (100 ng/0.1 mL): Mix 1.0 mL of QC 3 with 3.0 mL of blank colonic tissue homogenate. Store at −80° C. in 100 μL aliquots.
3. QC 1 (10 ng/0.1 mL): Mix 0.5 mL of QC 2 with 4.5 mL of blank colonic tissue homogenate. Store at −80° C. in 100 μL aliquots.

7.9. Sample Preparation

Plasma Samples

1. Place 100 μL of plasma (plasma blank, plasma STs, plasma QCs or patient plasma samples) into a 1.5 mL plastic centrifuge tube.
2. Add 50 μL of the working internal standard solution (1.0 μg/mL 6-TG-$^{13}C2$, $^{15}N$ in 0.1M HCl) and vortex briefly.
3. Add 0.9 mL of 10 mg/0.9 mL DL-dithiothreitol (DTT).
4. Add 100 μL of 70% perchloric acid and vortex for 30 s immediately.
5. Centrifuge at 15,000 g for 5 min.
6. Mix 50 μL of supernatant with 200 μL of 300 mM ammonium bicarbonate to neutralize the sample.
7. Inject 10 μL aliquots into LC-MS/MS.

RBC and Colonic Tissue Samples

Intracellular 6-thioguanine Nucleotides (6-TGN) is the major metabolite of 6-TG in cells. 6-TGN in RBC and in colonic tissue will be converted back to free 6-TG by acid hydrolysis with heating before the analysis of 6-TG concentrations to avoid underestimating the bioavailability.

RBC Samples

1. Centrifuge whole blood to isolate RBC.
2. Wash RBC twice in two volumes of saline and centrifuge at 1,250 g for 5 min.
3. Count the number of the washed RBC to normalize 6-TG concentration to 8x$10^8$ RBCs.
4. Place 100 μL of RBC (RBC blank, RBC STs, RBC QCs or patient RBC samples) into a 1.5 mL plastic centrifuge tube.

5. Add 50 μL of the working internal standard solution and vortex briefly.
6. Add 0.9 mL of 10 mg/0.9 mL DTT.
7. Add 100 μL of 70% perchloric acid and vortex for 30 s immediately.
8. Centrifuge at 15,000 g for 5 min.
9. Transfer 320 μL of the supernatant to a 96 plate, cover the plate with aluminium-foil sealing film, and heat in the Block Heater at 120° C. for 60 min.
10. Remove the aluminium-foil sealing film immediately and carefully.
11. After cooling, mix 50 μL of supernatant with 200 μL of 300 mM ammonium bicarbonate to neutralize the sample.
12. Inject 10 μL aliquots into LC-MS/MS.

Colonic Tissue Samples

1. Homogenization of Patient Tissue Samples
   Weigh colonic biopsy tissue.
   Add four-fold (w/w) cold PBS into the tube of colonic biopsy tissue sample to process the homogenization using the Omni Tissue Homogenizer.
2. Place 100 μL of tissue homogenate (tissue homogenate blank, tissue homogenate STs, QCs or patient tissue homogenate samples) into a 1.5 mL centrifuge tube.
3. Add 50 μL of the working internal standard solution and vortex briefly.
4. Add 0.9 mL of 10 mg/0.9 mL DTT.
5. Add 100 μL of 70% perchloric acid and vortex for 30 s immediately.
6. Centrifuge at 15,000 g for 5 min.
7. Transfer 320 μL of the supernatant to a 96 plate, cover the plate with aluminium-foil sealing film, and heat in the Block Heater at 120° C. for 60 min.
8. Remove the aluminium-foil sealing film immediately and carefully.
9. After cooling, mix 50 μL of supernatant with 200 μL of 300 mM ammonium bicarbonate to neutralize 5 the sample.
10. Inject 10 μL aliquots into LC-MS/MS.

Results

Results from the first two patients in the study are provided in Table 19.

TABLE 19

Results from Patients 1 and 2

| | Patient 1 | Patient 2 |
|---|---|---|
| Dose of 6-thioguanine in suppositories | 20 mg | 5 mg |
| Demographic information (sex and age band) | Female, 25-30 | Male, 30-35 |
| Concomitant IBD Medication | Pentasa (mesalazine) 2 g twice daily orally | None |
| Previous non-responsive IBD treatments | Pentasa (mesalazine) orally and rectally | Not known |
| Day 1 SCCAI | 10 | 6 |
| Day 8 SCCAI | 6 | 2 |
| Day 15 SCCAI | 4 | 2 |
| Day 22 SCCAI | 4 | 2 |
| Day 29 SCCAI | 5 | 4 |
| Starting Endoscopic subscore of the Mayo Score | 3 | 2 |
| Day 29 Endoscopic subscore of the Mayo Score | 1 | 2 |
| Starting UCEIS | 5 | 6 |
| Day 29 UCEIS | 2 | 5 |
| Day 1 Pharmacokinetics (PK) & tissue | See Table 20 below | See Table 20 below |
| Day 29 Pharmacokinetics (PK) & tissue | Not yet completed | Not yet completed |
| Any treatment emergent adverse events | None | None |

Ulcerative proctitis is an inflammatory bowel disease that causes inflammation and ulcers in the rectum area. The symptoms include diarrhea, urgency to defecate and rectal bleeding.

UCEIS (ulcerative colitis endoscopic index of severity) is based on three descriptors and is calculated as a simple sum: vascular pattern (scored 0-2); bleeding (scored 0-3); and erosions and ulcers (scored 0-3). The range of the UCEIS score is 0-8. The UCEIS score may be classified into the following categories: 0-1, remission; 2-4, mild disease activity; 5-6, moderate disease activity; 7-8 severe disease activity (see for example, Ikeya et al. J Crohns Colitis. 2016 March; 10(3): 286-295).

The Mayo endoscopic score (Mayo ES) has a range of 0-3 and may be classified into the following four categories: 0, normal or inactive disease; 1, mild disease with erythema, decreased vascular patterns and mild friability; 2, moderate disease with marked erythema, absence of vascular patterns, friability and erosions; 3, severe disease with spontaneous bleeding and ulceration (see for example, Ikeya et al. J Crohns Colitis. 2016 March; 10(3): 286-295).

SCCAI (simple clinical colitis activity index) is a questionnaire completed by patients which gives an indication of severity of colitis symptoms and activity or remission of disease. The questions are based on bowel frequency (day), bowel frequency (night), urgency of defecation, blood in stool, general well being and extracolonic features (for example musculoskeletal (e.g. arthritis), ocular (e.g. uveitis, episcleritis etc), dermatological (e.g. pyoderma gangrenosum, erythema nodosum etc), oral (aphthous stomatitis)). The score ranges from 0 to 20.

A SCCAI score of less than 2.5 is considered indicative of remission (see for example, Bewtra et al, "An Optimized Patient-reported Ulcerative Colitis Disease Activity Measure Derived from the Mayo Score and the Simple Clinical Colitis Activity Index", Inflamm Bowel Dis. 2014 June; 20(6): 1070-1078). A clinical response may be defined as a decrease in Simple Clinical Colitis Activity Index (SCCAI) score of greater than or equal to 3 from baseline (see for example, Crouwel at al. "Rectally Administrated Thioguanine for Distal Ulcerative Colitis: A Multicenter Case Series", Inflammatory Bowel Diseases, Volume 29, Issue 6, June 2023, pages 1000-1004).

Patient 1 received suppositories with a dose of 20 mg of 6-thiogunanine daily. Patient 1 had a more severe case of ulcerative proctitis with a starting SCCAI score of 10. Patient 1 had a clinical response, showing a decrease in SCCAI score of 4 points from baseline within 8 days and a decrease of 6 points from baseline within 15 days. The SCCAI score was maintained at 4 at day 22, but slightly increased to 5 by day 29. This was due to the patient experiencing a change from the loose stools associated with ulcerative proctitis to constipation with resulting abdominal bloating, discomfort, and straining at stool causing some ongoing bleeding. This pushed the SCCAI score falsely higher. A switch to constipation is not uncommon while ulcerative proctitis is being treated. The patient received separate treatment for constipation. The endoscopic appearance of the rectum showed very significant improvement with the endoscopic subscore of the Mayo Score dropping from 3 at the start of the trial to 1 by day 29. The UCEIS score also dropped from 5 at the start of the trial to 2 by day 29.

Patient 2 received suppositories with a dose of 5 mg of 6-thioguanaine daily. Despite receiving the low dose of 6-thioguanine the patient had a clinical response according to the SCCAI score and was in remission within only 8 days of starting treatment and remained in remission by day 15 and by day 22. The patient unfortunately had a deterioration in the SCCAI score at day 29 to 4. As with patient 1, symptoms and severity may vary over the course of treatment and may partially be due to outside factors, such as stress and lifestyle. The endoscopic appearance of the rectum showed improvement with the UCEIS score dropping from 6 at the start of the trial to 5 by day 29.

TABLE 20

Pharmacokinetics (PK) Day 1

| | Timing of sample | 6-TGN in RBC (pmol/8*10^8 RBC) | 6-TG in Serum (ng/mL) |
|---|---|---|---|
| Patient 1 | Pre-dose | <75 | 0.000 |
| (20 mg | 30 min | <75 | 0.713 |
| dose) | 1 hour | <75 | 1.190 |
| | 2 hour | <75 | 1.350 |
| | 4 hour | <75 | 2.030 |
| | 6 hour | <75 | 1.980 |
| Patient 2 | Pre-dose | <75 | 0.000 |
| (5 mg | 30 min | <75 | 0.000 |
| dose) | 1 hour | <75 | 0.000 |
| | 2 hour | <75 | 0.000 |
| | 4 hour | <75 | 0.000 |
| | 6 hour | <75 | 0.000 |

With reference to the results in Table 20, LLOQ (Lower Limit of Quantification) for 6-TGN in red blood cells (RBC) is 75 pmol/8*10^8 RBC. LLOQ for 6-TG in serum is 2.5 ng/ml. The 6-TG concentrations in serum below the LLOQ were obtained by extrapolation of standard curve below LLOQ, so these values may have a large variance. The analyst was blind to the patient/dosing.

The PK data in Table 20 was obtained from blood sampling taken prior to and after the first dose of the rectal suppository on day 1. The results should therefore not be considered steady state.

6-TGN was undetectable for both patients/doses on Day 1.

6-TG was detectable in serum in patient 1 (20 mg dose) but below limit of quantification and so results may have a large variance. 6-TG was not detectable in patient 2 (5 mg dose) which may be consistent with lower dose and/or the mucosa of the patient may not have been as inflamed as in patient 1 allowing less direct drug transfer into blood.

While the invention has been described in detail and with reference to specific examples thereof, it will be apparent to one skilled in the art that various changes and modifications can be made therein without departing from the spirit and scope thereof.

The invention claimed is:

1. A rectal suppository comprising:

about 1 to 30 mg of 6-thioguanine, about 80 to 99.9% w/w of at least one hard fat, wherein the hard fat comprises less than about 10 mole % of one or more unsaturated fatty acid(s) and has a hydroxyl value of less than 40 mg KOH/g, about 0.1 to 20% w/w of at least one surfactant, and about 0.25 to 1% w/w of a suspending agent, wherein one surfactant is polysorbate 80.

2. The suppository of claim 1 wherein the suppository comprises about 5 to 20 mg of 6-thioguanine.

3. The suppository of claim 1 wherein the suppository comprises about 90 to 99.5% w/w of the hard fat.

4. The suppository of claim 1 wherein the suppository comprises about 0.1 to 5% w/w of the surfactant.

5. The suppository of claim 1 wherein the surfactant additionally comprises from any one or more a polyoxyethylene derivative of natural or hydrogenated vegetable oil(s), a alkyl/dialykyl sulfate, sulfonate or sulfosuccinate salt, a polyoxyethylene fatty acid ester, a phospholipid, a transesterification product of natural vegetable oil triglyceride and polyalkylene polyol, a sorbitan fatty acid ester, a pentaerythritol fatty acid ester, a polyoxyethylene glycol alkyl ether and/or ester, a sucrose ester, an ethoxylated fatty alcohol, or a fatty acid salt.

6. The suppository of claim 1 wherein the suspending agent is selected from one or more of: silicon dioxide, a clay, aluminum monostearate and magnesium stearate.

7. The suppository of claim 1 wherein the suppository comprises an antioxidant.

8. The suppository of claim 1 wherein the suppository has a total weight of about 800 to about 3000 mg.

9. A method of treating inflammatory bowel disease in a subject, the method comprising administering a rectal suppository comprising:

about 1 to 30 mg of 6-thioguanine, about 80 to 99.9% w/w of at least one hard fat, wherein the hard fat comprises less than about 10 mole % of one or more unsaturated fatty acid(s) and has a hydroxyl value of less than 40 mg KOH/g, about 0.1 to 20% w/w of at least one surfactant, and about 0.25 to 1% w/w of a suspending agent, to the subject in need thereof, wherein one surfactant is polysorbate 80.

10. The method of claim 9 wherein the inflammatory bowel disease effects the rectum.

11. The method of claim 9 wherein the inflammatory bowel disease is ulcerative colitis or Crohn's disease, effecting the rectum.

12. The method or use of claim 11 wherein the ulcerative colitis is ulcerative proctitis, proctosigmoiditis, and/or left-sided colitis.

13. The suppository of claim 1 wherein the 6-thioguanine in the suppository has a particle size distribution of D50 of less than about 100 μm.

14. The suppository of claim 1 wherein the surfactant has a melting point below 35° C.

15. The suppository of claim 1 wherein the suppository has a melting range of about 33 to 38° C.

16. The suppository of claim 1 wherein the suppository exhibits release of the 6-thioguanine in vitro in dissolution medium that corresponds to:

(a) about 20 to about 100% of the 6-thioguanine at about 20 minutes from placement of the suppository in the dissolution medium, (b) not less than about 40% of the 6-thioguanine at about 60 minutes from placement of the suppository in the dissolution medium, wherein the dissolution medium is 0.05 M phosphate buffer with a pH 6.8±0.05, at 37.0° C.±0.5° C.

17. The suppository of claim 1 wherein the suppository exhibits release of the 6-thioguanine in vitro in dissolution medium that corresponds to:

(a) about 60 to about 100% of the 6-thioguanine at about 20 minutes from placement of the suppository in the dissolution medium, (b) not less than about 80% of the 6-thioguanine at about 60 minutes from placement of the suppository in the dissolution medium, wherein the dissolution medium is 0.05 M phosphate buffer with a pH 6.8±0.05, at 37.0° C.±0.5° C.

* * * * *